US010260114B2

(12) United States Patent
Chen et al.

(10) Patent No.: US 10,260,114 B2
(45) Date of Patent: Apr. 16, 2019

(54) CRYSTALLINE LANTHANUM-CARBOXYLATE COORDINATION POLYMERS AND THEIR USE

(71) Applicants: Southern Medical University, Guangzhou (CN); Macau University of Science and Technology, Taipa (MO)

(72) Inventors: Jin-Xiang Chen, Guangzhou (CN); Bin Sun, Guangzhou (CN); Bao-Ping Xie, Guangzhou (CN); Zhi-Hong Jiang, Taipa (MO); Li-Ping Bai, Taipa (MO)

(73) Assignees: MACAU UNIVERSITY OF SCIENCE AND TECHNOLOGY, Taipa (MO); SOUTHERN MEDICAL UNIVERSITY, Guangzhou (CN)

( * ) Notice: Subject to any disclaimer, the term of this patent is extended or adjusted under 35 U.S.C. 154(b) by 0 days.

(21) Appl. No.: 15/598,434

(22) Filed: May 18, 2017

(65) Prior Publication Data

US 2018/0334733 A1 Nov. 22, 2018

(51) Int. Cl.
| | | |
|---|---|---|
| C07D 213/50 | (2006.01) |
| C12Q 1/70 | (2006.01) |
| C12Q 1/6818 | (2018.01) |
| C08G 79/00 | (2006.01) |

(52) U.S. Cl.
CPC .............. *C12Q 1/701* (2013.01); *C08G 79/00* (2013.01); *C12Q 1/6818* (2013.01)

(58) Field of Classification Search
CPC .................................................... C07D 213/50
USPC ......................................................... 546/321
See application file for complete search history.

(56) References Cited

FOREIGN PATENT DOCUMENTS

CN        201510952885 A  *  5/2016  ........... C08G 83/008

OTHER PUBLICATIONS

Chemical Thermodynamics ata Glace; H. Donald Brooke Jenkins; (2008); Chapter 49: Le Chatelier's Principle pp. 160-163. (https://onlinelibrary.wiley.com/doi/pdf/10.1002/9780470697733.ch49, last accessed Sep. 5, 2018).*
Y. C. Cao et al, "Nanoparticles with Raman Spectroscopic Fingerprints for DNA and RNA Detection", Science, 2002, 297, 1536.
X. Zhu et al, "Metal-organic framework (MOF): a novel sensing platform for biomolecules", Chem. Commun., 2013, 49, 1276.
L. Chen et al, "Metal-organic frameworks-based biosensor for sequence-specific recognition of double-stranded DNA". Analyst., 2013, 138, 3490.
C. Song et al, "A barium based coordination polymer for the activity assay of deoxyibonuclease", Chem Commun, 2014, 50, 11177.
Y. Wu et al, "Nano Metal-Organic Framework (NMOF)-Based Strategies for Multiplexed MicroRNA Detection in Solution and Living Cancer Cells", Nanoscale, 2015, 7, 1753.
J. Tian et al, "Rapid, sensitive, and selective fluorescent DNA detection using iron-based metal-organic framework nanorods: Synergies of the metal center and organic linker", Biosensors and Bioelectronics., 2015, 71, 1.
C. Zhao et al, "Targeting Human Telomeric Higher-Order DNA: Dimeric G-Quadruplex Units Serve as Preferred Binding Site", J. Am. Chem. Soc., 2013, 135, 18786.
J. M. Fang et al, "Metal-organic framework MIL-101 as a low background signal platform for label-free DNA detection", Analyst, 2014, 139, 801.
J. W. Zhang et al, "Water-stable metal-organic frameworks with intrinsic peroxidase-like catalytic activity as a colorimetric biosensing platform", Chem. Comm., 2014, 50, 1092.
Z. X. Zhang et al, "Stitching 2D Polymeric Layers into Flexible Interpenetrated Metal-Organic Frameworks within Single Crystals", Angew. Chem. Int. Ed. 2014, 53, 1.
S. P. Yang et al, "Platforms Formed from a Three-Dimensional Cu-Based Zwitterionic Metal-Organic Framework and Probe ss-DNA: Selective Fluorescent Biosensors for Human Immunodeficiency Virus 1 ds-DNA and Sudan Virus RNA Sequences", Anal Chem., 2015, 87, 12206.
L. Qin et al, "A water-stable metal-organic framework of a zwitterionic carboxylate with dysprosium: a sensing platform for Ebolavirus RNA sequences", Chem. Commun., 2016, 52, 132.
H. Q. Zhao et al, "A zwitterionic 1D/2D polymer co-crystal and its polymorphic sub-components: a highly selective sensing platform for HIV ds-DNA sequences", Dalton. Trans., 2016, 45, 5092.
M. Chen et al "Five water-soluble zwitterionic copper(II)-carboxylate polymers: role of dipyridyl coligands in enhancing the DNA-binding, cleaving and anticancer activities", Dalton. Trans., 2015, 44, 13369.
J. X. Chen et al, "Transmetalation of a Dodecahedral Na9 Aggregate-Based Polymer: A Facile Route to Water Stable Cu(II) Coordination Networks", Inorg. Chem., 2014, 53, 7446.
L. J. Farrugia, "Computer Program Abstracts", J. Appl. Crystallogr., 1999, 32, 837.
A. L. Spek, "Structure validation in chemical crystallography". Acta. Crystallogr. D. Biol. Crystallogr., 2009, 65, 148.
J. Atchison et al, "Modulation of ROS production in photodynamic therapy using a pH controlled photoinduced electron transfer (PET) based sensitizer", Chem. Commun., 2015, 51, 16832.
G. W. Zhang et al, "Interaction of alpinetin with bovine serum albumin: Probing of the mechanism and binding site by spectroscopic methods", Spectrochim. Acta. A. Mol. Biomol. Spectrosc., 2010, 76, 410.
B. Rauzan et al, "Kinetics and Thermodynamics of DNA, RNA and Hybrid Duplex Formation". Biochemistry, 2013, 52, 765.
R. J. Hunter, "Zeta Potential in Colloid Science: Principles and Applications", Academic Press, 2013.

(Continued)

*Primary Examiner* — Jeffrey H Murray
(74) *Attorney, Agent, or Firm* — Renner Kenner Greive Bobak Taylor & Weber

(57) ABSTRACT

The present invention relates in a first aspect to a method of preparing a crystalline lanthanum-carboxylate coordination polymer and the crystalline lanthanum-carboxylate coordination polymer obtained or obtainable by the method. In another aspect of the present invention, also provides a method of detecting a target nucleic acid sequence in a sample.

7 Claims, 14 Drawing Sheets
(4 of 14 Drawing Sheet(s) Filed in Color)

Specification includes a Sequence Listing.

(56) References Cited

OTHER PUBLICATIONS

J. M. Goldberg et al, "Thioamide Quenching of Fluorescent Probes through Photoinduced Electron Transfer: Mechanistic Studies and Applications", J. Am. Chem. Soc., 2013, 135, 18651.

J. F. Guo et al, "Metal-organic framework MIL-101 enhanced fluorescence anisotrophy for sensitive detection of DNA", RSC. Adv., 2014, 4, 9379.

J. H. Liu et al, "Graphene Signal Amplification for Sensitive and Real-Time Fluorescence Anisotrophhy Detection of Small Molecules", Anal. Chem., 2013, 85, 1424.

J. J. Liu et al, "Nanoscale metal-organic frameworks for combined photdynamic & radiation therapy in cancer treatment", Biomaterials., 2016, 97, 1.

\* cited by examiner

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthesized

<400> SEQUENCE: 1
ttaaaaagtt tgtcctcatc                                              20

<210> SEQ ID NO 2
<211> LENGTH: 20
<212> TYPE: RNA
<213> ORGANISM: Artificial Sequence
<220> FEATURE:
<223> OTHER INFORMATION: Synthesized

<400> SEQUENCE: 2
gaugaggaca aacuuuuuaa                                              20

<210> SEQ ID NO 3
<211> LENGTH: 30
<212> TYPE: RNA
<213> ORGANISM: Artificial Sequence
<220> FEATURE:
<223> OTHER INFORMATION: Synthesized

<400> SEQUENCE: 3
ucuuccguuu gaugaggaca aacuuuuuaa                                   30

<210> SEQ ID NO 4
<211> LENGTH: 40
<212> TYPE: RNA
<213> ORGANISM: Artificial Sequence
<220> FEATURE:
<223> OTHER INFORMATION: Synthesized

<400> SEQUENCE: 4
augaugguga ucuuccguuu gaugaggaca aacuuuuuaa                        40

<210> SEQ ID NO 5
<211> LENGTH: 20
<212> TYPE: RNA
<213> ORGANISM: Artificial Sequence
<220> FEATURE:
<223> OTHER INFORMATION: Synthesized

<400> SEQUENCE: 5
gaugaggaca cacuuuuuaa                                              20

<210> SEQ ID NO 6
<211> LENGTH: 20
<212> TYPE: RNA
<213> ORGANISM: Artificial Sequence
<220> FEATURE:
<223> OTHER INFORMATION: Synthesized

<400> SEQUENCE: 6
ggcaaucagc uggacacaug                                              20

CRYSTALLINE LANTHANUM-CARBOXYLATE COORDINATION POLYMERS AND THEIR USE

SEQUENCE LISTING

The Sequence Listing file entitled "sequencelisting" having a size of 1,383 bytes and a creation date of 18 May 2017 that was filed with the patent application is incorporated herein by reference in its entirety.

TECHNICAL FIELD

The present invention relates to a method of preparing a crystalline lanthanum-carboxylate coordination polymer comprising and especially preferably essentially consisting of lanthanum-carboxylate coordination entities and the crystalline lanthanum-carboxylate coordination polymer obtained or obtainable by said method. Preferably but not exclusively, the crystalline lanthanum-carboxylate coordination polymer comprises repeating coordination entities extending in two (2D) or three (3D) dimensions. Still further, the present invention provides a method of detecting a target nucleic acid sequence in a sample. The target nucleic acid sequence is in particular from a viral RNA, in particular it is Sudan virus RNA. Further provided is a kit, which comprises the crystalline lanthanum-carboxylate coordination polymer and an oligonucleotide probe and its use.

BACKGROUND OF THE INVENTION

Ebolavirus (EBOV) is a human epidemics associated with four sub-species, namely Bundibugyo virus (BDBV), Reston virus (RESTV), Sudan virus (SUDV) and TM Forest virus (TAFV). Among them, SUDV induces 50% fatality rate and longer progression to death. SUDV is a filamentous RNA virus that causes Ebola viral hemorrhagic fever (VHF), a severe and often fatal to human and non-human primates. Unfortunately, there is currently no effective drug or vaccine available against this type of virus. Thus, early diagnosis for such RNA virus is essential for its surveillance and control.

Many efforts have been made to develop fluorescence assays for nucleic acid detection. The general mechanism used in such approach lies in the absorption of the fluorophore-labeled probe single-stranded DNA (ss-DNA, also referenced as probe DNA; P-DNA) by nano-material to form a conjugate and accompanied by substantial fluorescence quenching. Following the specific hybridization with its target disease related DNA or RNA sequences, the formed double-stranded DNA (ds-DNA) or ds-DNA/RNA becomes more rigid and detaches from the surface of the nano-material with the recovery of fluorescence. Up to now, a handful of nano-materials including gold nanoparticles, single-walled carbon nanotubes and graphene have been successfully used in such assay, and most of these nano-materials are able to detect DNA or RNA at the nanomolar level.

Recently, a few of organic frameworks (MOFs) have been explored as fluorescence quenching platform for the detection of target DNA/RNA (e.g., Zhu, X. et al., Chem. Commun., 2013, 49, 1276; Chen, L. et al., Analyst., 2013, 138, 3490; Wang, G. Y. et al., J. Mater. Chem. A, 2014, 2, 2213; Wu, Y. et al., Nanoscale, 2015, 7, 1753; Tian, J. et al., Biosens. Bioelectron., 2015, 71, 1; Zhao, C. et al., J. Am. Chem. Soc., 2013, 135, 18786, Zhang, Z. X. et al., Angew. Chem. Int. Ed. 2014, 53, 4628; Yang, S. P. et al., Anal Chem., 2015, 87, 12206). Most studied MOFs are based on previously reported water stable nano-MOF, such as MIL-101 (Fang, J. M. et al., Analyst, 2014, 139, 801), MIL-88B (Tian, J. Q. et al., Biosens. Bioelectron., 2015, 71, 1), UiO-66 (Wu, Y. et al., Nanoscale, 2015, 7, 1753), UiO-66-$NH_2$ (Zhang, H. T. et al., Chem. Commun., 2014, 50, 12069) and etc. However, such development is still at an infant stage and provided MOFs often suffer from a poor water stability and/or poor water stability significantly limiting their diagnostic use as a sensing platform.

Accordingly, there is a strong need for improved compounds which are easily obtainable in an economic way with sufficient water stability, water solubility and sufficient DNA or RNA binding ability which are suitable to form sensing platforms for target nucleic acid sequences such as in the diagnosis of viral infectious diseases and in particular Ebolavirus infections.

SUMMARY OF THE INVENTION

The first aspect of the present invention relates to a method of preparing a crystalline lanthanum-carboxylate coordination polymer, the lanthanum being in particular of the oxidation state +3. Said method of the present invention comprises steps of:

(i) preparing a mixture comprising lanthanum ions and a pyridyl ligand which pyridyl ligand is a quaternized carboxylate pyridyl ligand and optionally subjecting the mixture to conditions under which a precipitate is formed and separating the precipitate;

(ii) subjecting the mixture of step (i) or the precipitate of step (i) to conditions under which crystals of the lanthanum-carboxylate coordination polymer are formed;

(iii) separating the crystals of the lanthanum-carboxylate coordination polymer from the mixture.

The first pyridyl ligand preferably has a structure of Formula (I):

Formula (I)

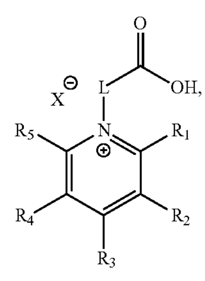

X is a halogen. Two of $R^1$ to $R^5$ are a group of Formula (II)

Formula (II)

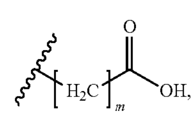

m is an integer and selected from 0, 1 or 2. The other of $R^1$ to $R^5$ are hydrogen. L is a linking group selected from an alkyl group, an aralkyl group, an alkaryl group, an alkarylalkyl or an aryl.

The pyridyl ligand has more preferably a structure of Formula (III):

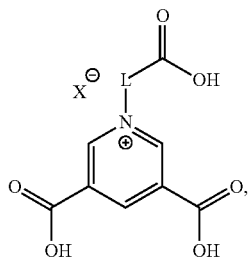

Formula (III)

with X and L being as defined above.

In particular, the pyridyl ligand has a structure of Formula (IV):

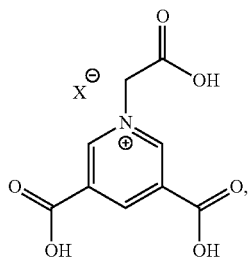

Formula (IV)

or of Formula (V):

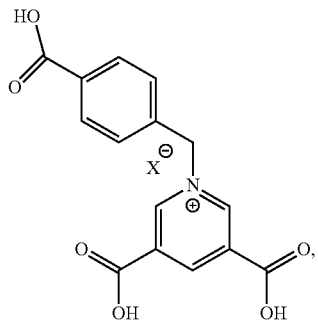

Formula (V)

with X being as defined as above.

The present invention further provides a crystalline lanthanum-carboxylate coordination polymer obtained or obtainable by the method described above. The crystalline lanthanum-carboxylate coordination polymer in particular extends through repeating coordination entities in two or three dimensions.

The present invention in a third aspect provides a method of detecting a target nucleic acid sequence in a sample such as blood. Said method of the present invention comprises steps of:

(i) preparing a mixture of a crystalline lanthanum-carboxylate coordination polymer obtained or obtainable with the preparation method described above and an oligonucleotide probe having a nucleic acid sequence at least partially complementary to said target nucleic acid sequence and being labeled with a fluorescent;

(ii) incubating the mixture with the sample;

(iii) measuring the fluorescence after step (ii);

(iv) determining the presence and/or amount of the target nucleic acid sequence in the sample based on the fluorescence determined in step (iii).

The target nucleic acid sequence is in particular viral RNA such as from Ebolavirus, in particular from Sudan virus such as SUDV RNA comprising or in particular consisting of a sequence having SEQ. ID. NO:2, NO:3 or NO:4. Said oligonucleotide probe is labeled with a fluorescent, in particular FAM (fluorescein) is attached to the oligonucleotide probe. The oligonucleotide probe is in particular a FAM-labeled ss-DNA sequence comprising or consisting of SEQ. ID. NO:1.

The method and the crystalline lanthanum-carboxylate coordination polymer can in particular be used in the diagnosis of Ebolavirus such as Sudan virus infections.

Still further, a kit is provided with the present invention comprising:

(i) a crystalline lanthanum-carboxylate coordination polymer obtained or obtainable with the preparation method described above;

(ii) an oligonucleotide probe having a nucleic acid sequence complementary to a target nucleic acid sequence and being labeled with a fluorescent, in particular the oligonucleotide probe is a FAM-labeled oligonucleotide probe of SEQ. ID. NO:1.

In a further aspect, the present invention refers to the use of the crystalline lanthanum-carboxylate coordination polymer obtained or obtainable by the preparation method as described above or the kit in the diagnosis of viral infectious diseases, preferably of Ebolavirus, in particular Sudan virus infections. More specifically, the present invention refers to the use of the crystalline lanthanum-carboxylate coordination polymer or the kit for detecting the presence and/or the amount of a target nucleic acid in a sample from a subject such as a human, in particular Sudan virus RNA comprising or consisting of SEQ. ID. NO:2, NO:3 or NO:4.

The method of the present invention allows for preparing crystalline lanthanum-carboxylate coordination polymers. In particular, the inventors found that $\{[La_4(Cmdcp)_6(H_2O)_9]\}_n$ (also referenced as compound 1) with a three-dimensional (3D) structure and $\{[La_2(Cbdcp)_3(H_2O)_{10}]\}_n$ (also referenced as compound 2) with a 2D structure are highly water-soluble and water-stable and highly advantageous as sensing platforms for the detection of Ebolavirus, in particular Sudan virus RNA sequences. More specifically, compound 1 proved to have a porous framework that the edge of its channel is embroidered with positively charged quaternary ammonium nitrogen atoms, while compound 2 demonstrated a 2D layer structure with aromatic rings, positively charged pyridinium and free carboxylates on its surface. All these structural characteristics contribute to the interactions toward ss-DNA to form conjugates as sensing platforms.

These compounds proved to be able to strongly absorb carboxyfluorescein (FAM) labeled probe DNA (P-DNA) of SEQ. ID. NO:1 resulting in fluorescence quenching of FAM via a photo-induced electron transfer (PET) process leading to sensing platforms especially suitable for detection of Sudan virus RNA sequences. These two sensing platforms proved to be especially suitable to distinguish conservative linear single stranded RNA sequences of Sudan virus with high selectivity giving detection limits as low as 112 and 67 μM at a signal-to-noise ratio of 3. They also exhibited high specificity and can discriminate down to single-base mismatch RNA sequences.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows the PXRD pattern of compound 1. FIG. 1B shows the PXRD pattern of compound 2. FIG. 1C shows the weight loss of compounds 1 and 2 under various temperatures.

FIG. 6A shows the fluorescence spectra of P-DNA incubated with compound 1. FIG. 6B shows fluorescence spectra of P-DNA incubated with compound 2.

FIG. 7A shows the fluorescence quenching efficiency of the P-DNA by compounds 1, 2, La(NO$_3$)$_3$, H$_3$CbdcpBr, and H$_3$CmdcpBr at varying concentrations. FIG. 7B shows the fluorescence quenching efficiency of the P-DNA (50 nM) by compounds 1, 2, La(NO$_3$)$_3$, H$_3$CbdcpBr, and H$_3$CmdcpBr at the fixed concentration.

FIG. 8A shows the fluorescence intensity of P-DNA@1. FIG. 8B shows the fluorescence intensity of P-DNA@2.

FIG. 9A shows the fluorescence intensity of P-DNA@1. FIG. 9B shows the fluorescence intensity of P-DNA@2.

FIG. 10A shows the fluorescence recovery of P-DNA@1 systems by target $T_{20}$, $T_{30}$, $T_{40}$, $T_1$, $T_2$ and $T_{40A}$ at the fixed concentration. FIG. 10B shows the fluorescence recovery of P-DNA@1 systems by target $T_{20}$, $T_{30}$, $T_{40}$, $T_1$, $T_2$ and $T_{40A}$ at varying concentrations. FIG. 10C shows the fluorescence recovery of P-DNA@2 systems by target $T_{20}$, $T_{30}$, $T_{40}$, $T_1$, $T_2$ and $T_{40A}$ at the fixed concentration. FIG. 10D shows the fluorescence recovery of P-DNA@2 systems by target $T_{20}$, $T_{30}$, $T_{40}$, $T_1$, $T_2$ and $T_{40A}$ at varying concentrations.

FIG. 11A refers to compound 1. FIG. 11B refers to compound 2.

FIG. 12A refers to compound 1. FIG. 12B refers to compound 2.

DETAILED DESCRIPTION OF THE INVENTION

Figure 1A:
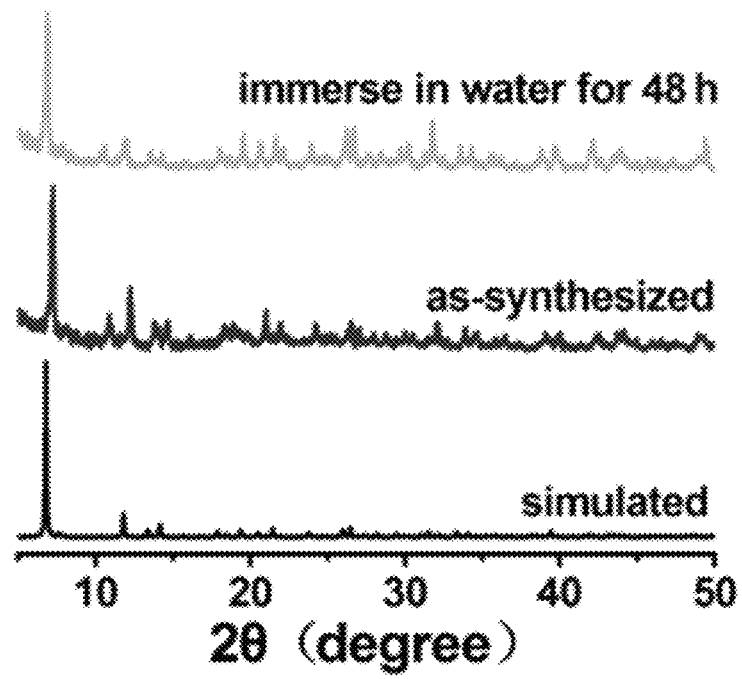
FIGS. 1A, 1b, and 1C shows powder X-ray diffraction (PXRD) patterns of compounds 1 and 2 showing agreement among the simulated, as-synthesized and of the compounds immersed in $H_2O$ for 48 h and the weight loss of compounds 1 and 2 in percentage in a thermogravimetric analysis.
Figure 1B:
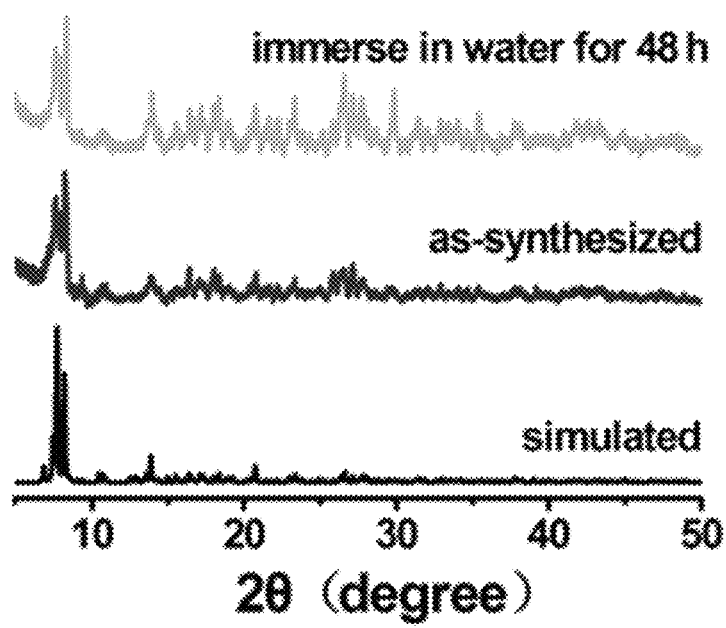
Figure 1C:
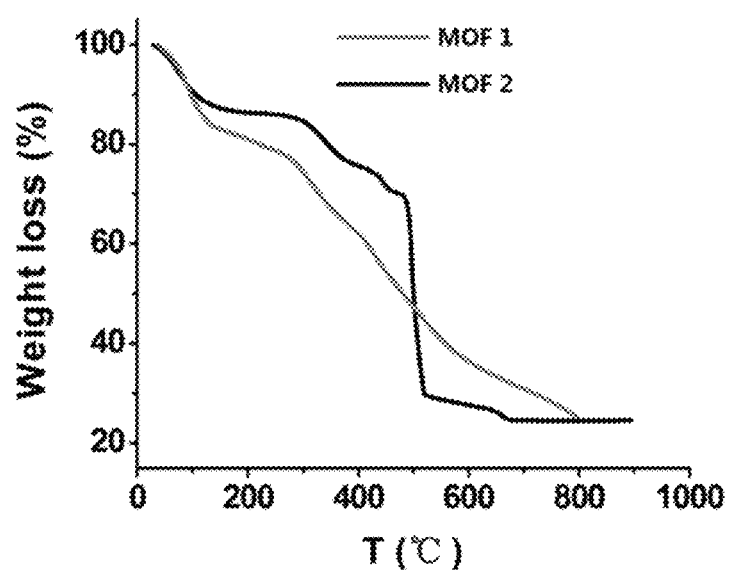
Figure 2A:
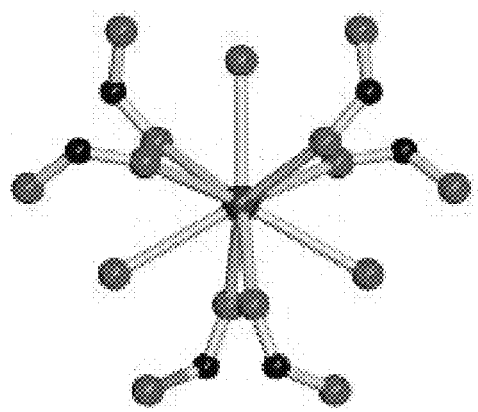
FIGS. 2A, 2B, 2C, and 2D illustrate the coordination environment (La(1) (FIG. 2A), La(2) (FIG. 2C)) and coordination geometry (La(1) (FIG. 2B), La(2) (FIG. 2D)) of La(III) ions in compound 1. Only carboxylate groups and La(III) ions (FIGS. 2A and 2C) or only oxygen atoms and La(III) ions were kept for clarity. Color codes: La(1) (dark red), La(3) (teal), O (red), C (black).
Figure 2B:
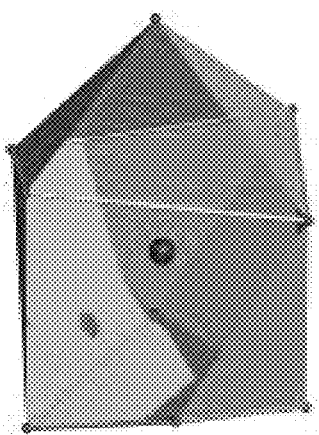
Figure 2C:
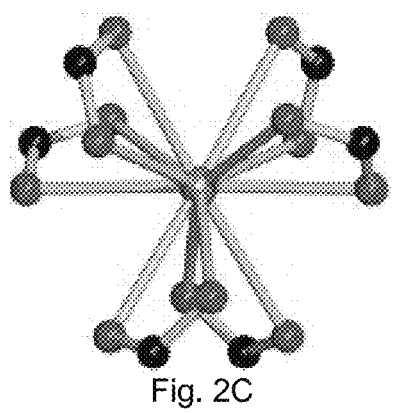
Figure 2D:
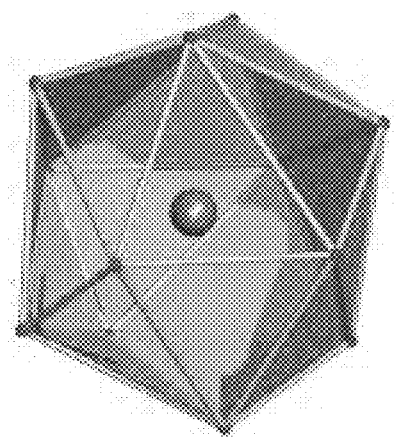
Figure 3A:
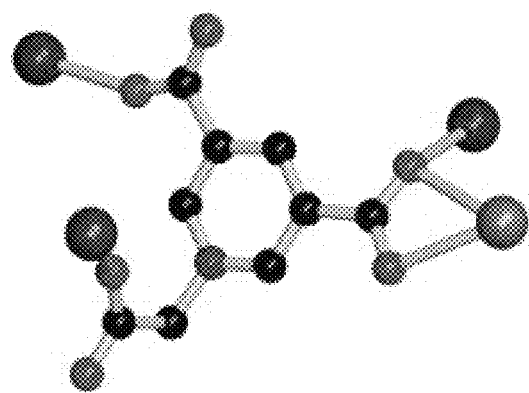
FIG. 3A illustrates the linking of the Cmdcp ligand in the asymmetric unit to four La(III) centers in a different fashion. Color codes: La(1) (dark red), La(2) (teal), La(3) (blue), O(red), C (black).
Figure 3B:
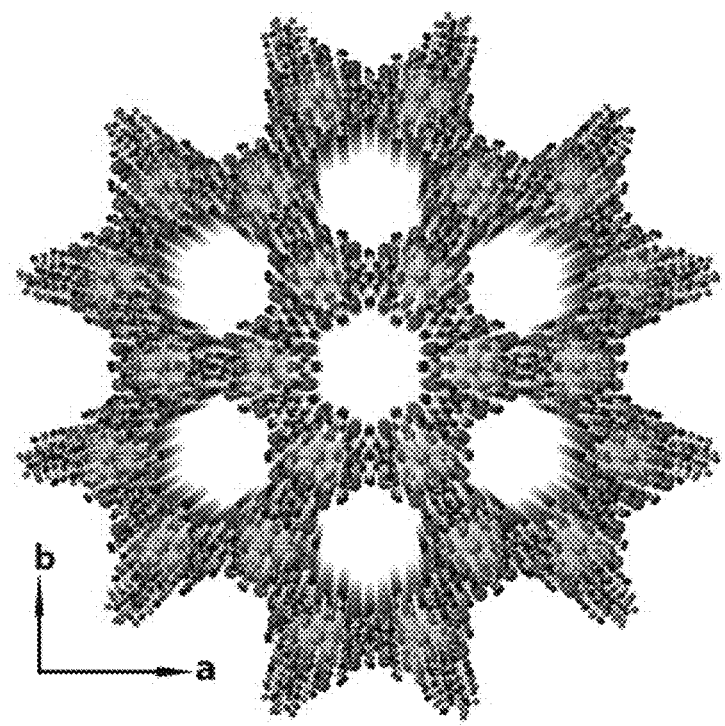
FIG. 3B illustrates the 3D structure of compound 1 viewed down the c axis and the free $H_2O$ was omitted for clarity. Color codes: La (green), O(red), C (black).
Figure 4:
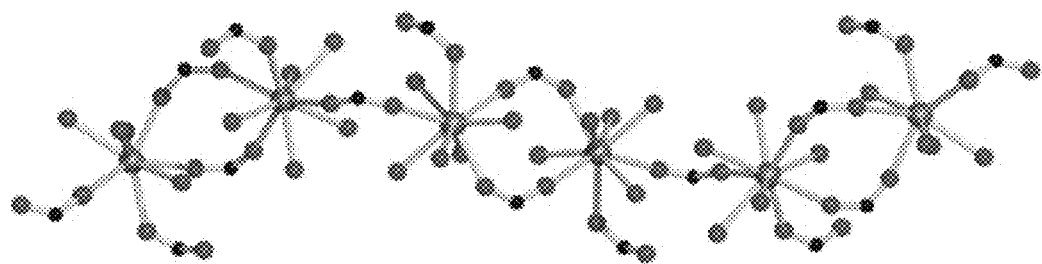
FIG. 4 shows the one-dimensional chain of La(III) units with only the La(III) ions, bridging carboxylate moieties containing ligands and coordination water molecules shown for clarity. Color codes: La (teal), O(red), N (blue), C (black).
Figure 5A:
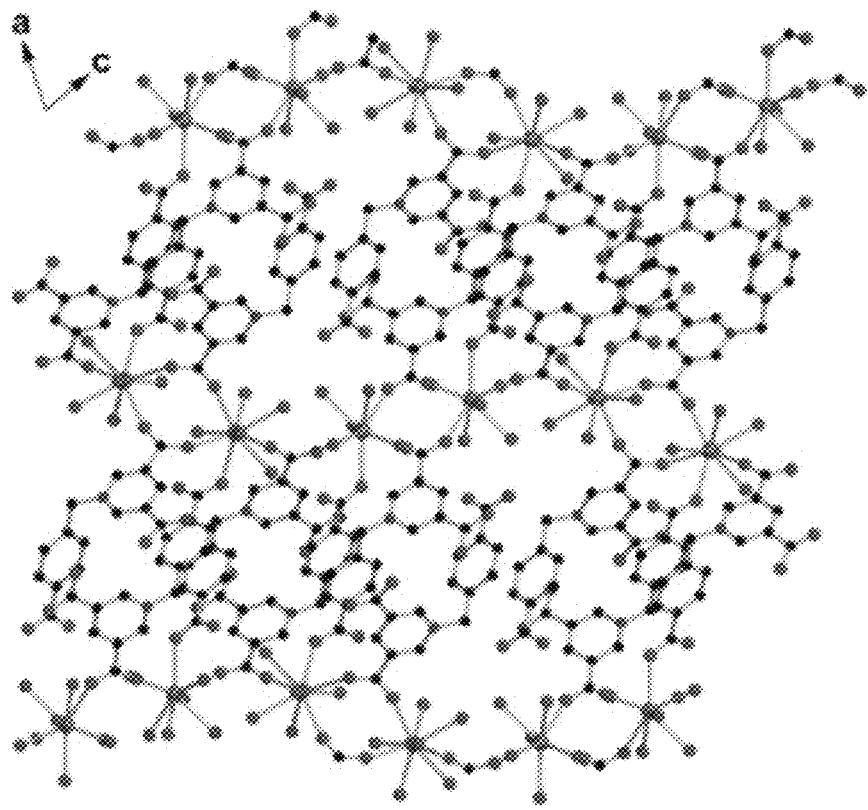
FIGS. 5A and 5B illustrate the structure of compound 2 showing the 2D plane structure and the plicated net while imagining Cbdcp ligands as the netting twine. Color codes: La (teal), O(red), N (blue), C (black).
Figure 5B:
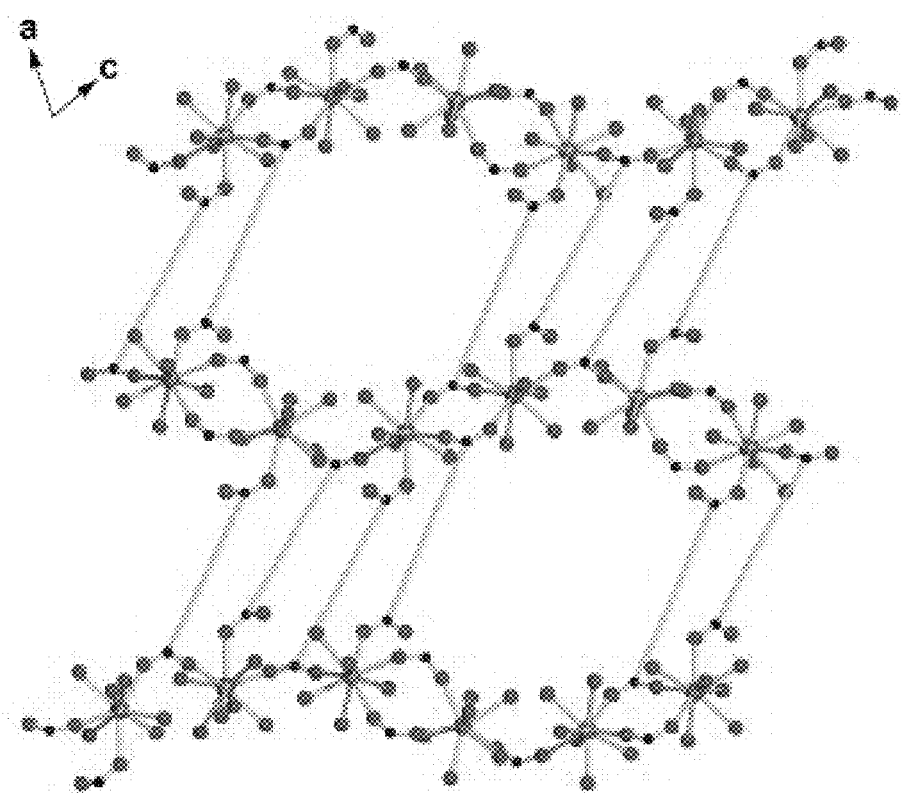
Figure 6A:
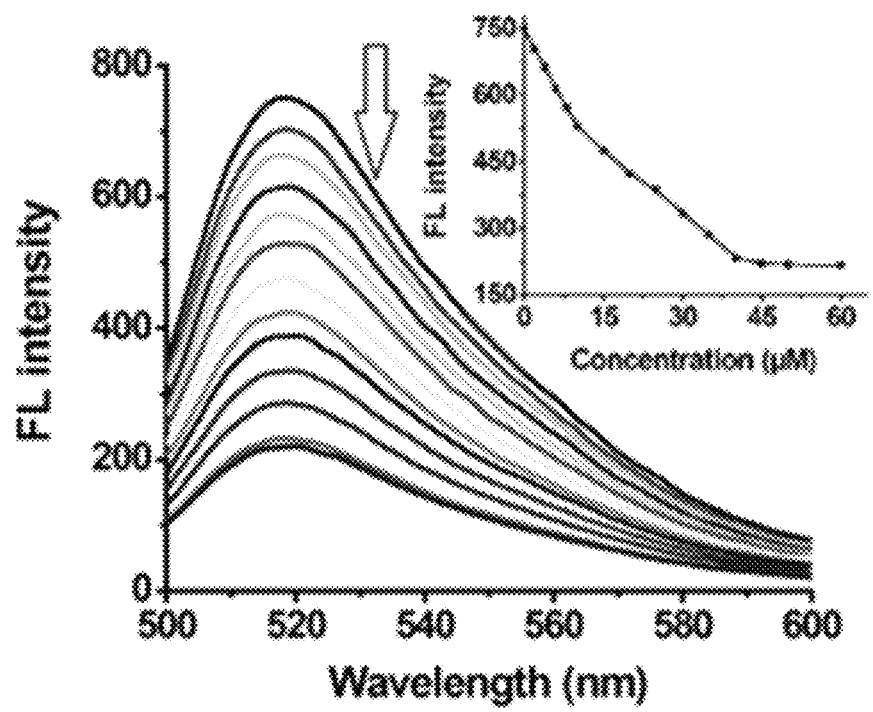
FIGS. 6A and 6B show fluorescence spectra of P-DNA (50 nM) incubated with compound 1 or 2 with varying concentrations. Inset: plot of the fluorescence intensity at 518 nm versus the concentrations of the compounds.
Figure 6B:
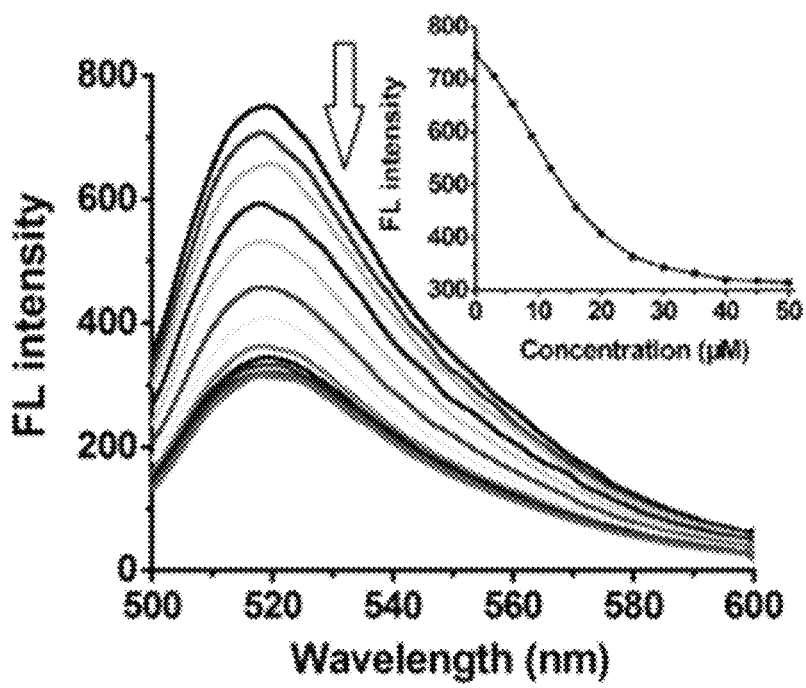
Figure 7A:
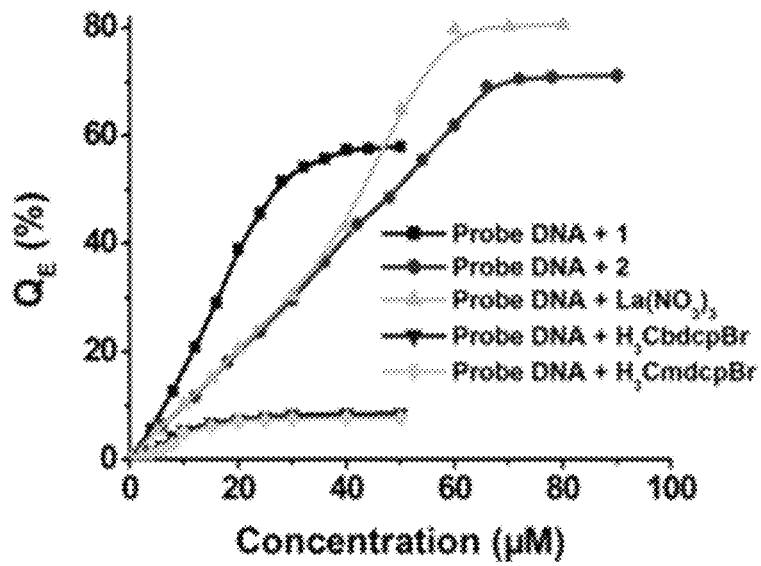
FIGS. 7A and 7B show the fluorescence quenching efficiency of the P-DNA (50 nM) by compounds 1, 2, La(NO$_3$)$_3$, H$_3$CbdcpBr, and H$_3$CmdcpBr at varying concentrations and at the fixed concentration of 50 µM in 100 µM Tris-HCl buffer (pH 7.4) at room temperature.
Figure 7B:
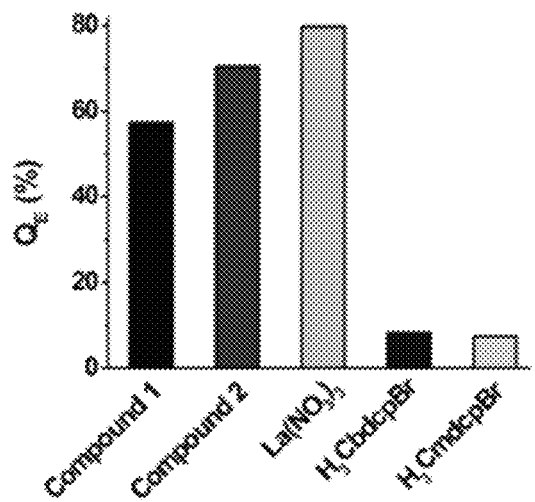
Figure 8A:
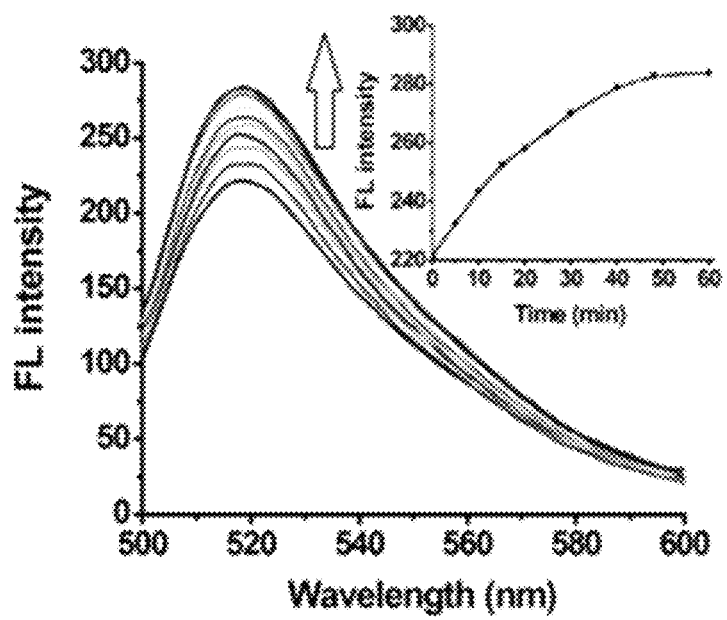
FIGS. 8A and 8B show the fluorescence intensity of P-DNA@1 (50 nM/45 µM) or P-DNA@2 (50 nM/40 µM) in the presence of target SUDV RNA sequences $T_{20}$ (25 nM) of varying incubation time. Insets: plots of fluorescence intensity at 518 nm versus the incubation time for target SUDV RNA sequences $T_{20}$.
Figure 8B:
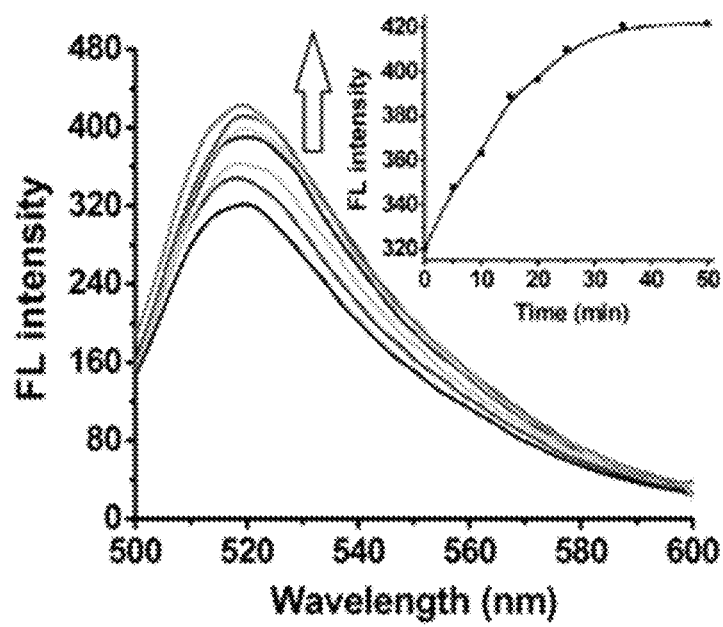
Figure 9A:
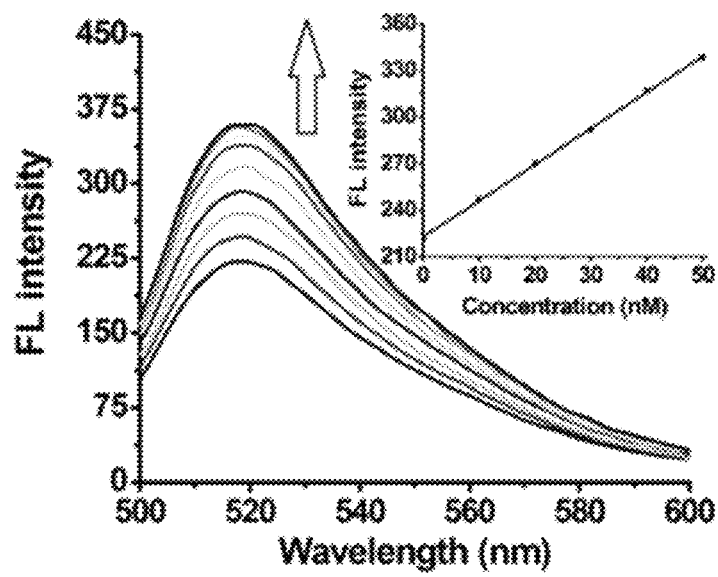
FIGS. 9A and 9B show the fluorescence spectra of the P-DNA@compound system (50 nM/45 µM for P-DNA@1 and 50 nM/40 µM for P-DNA@2) incubated with $T_{20}$ of varying concentrations. Inset: plot of the fluorescence intensity at 518 nm versus the concentrations of $T_{20}$.
Figure 9B:
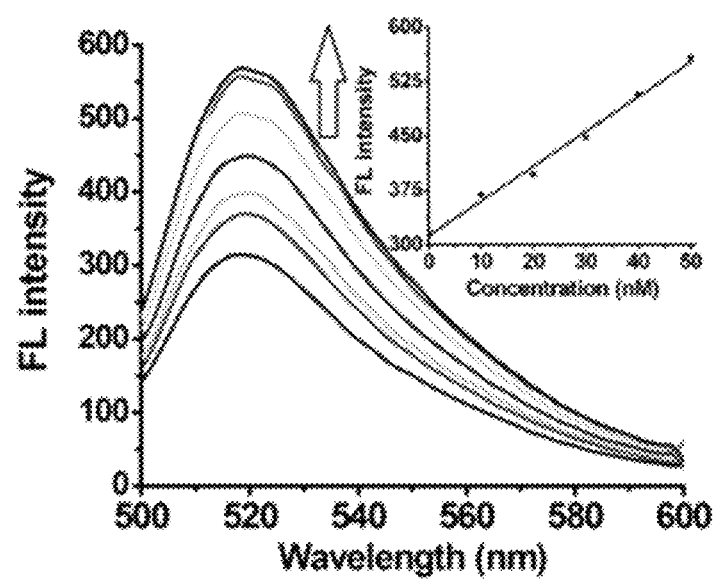
Figure 10A:
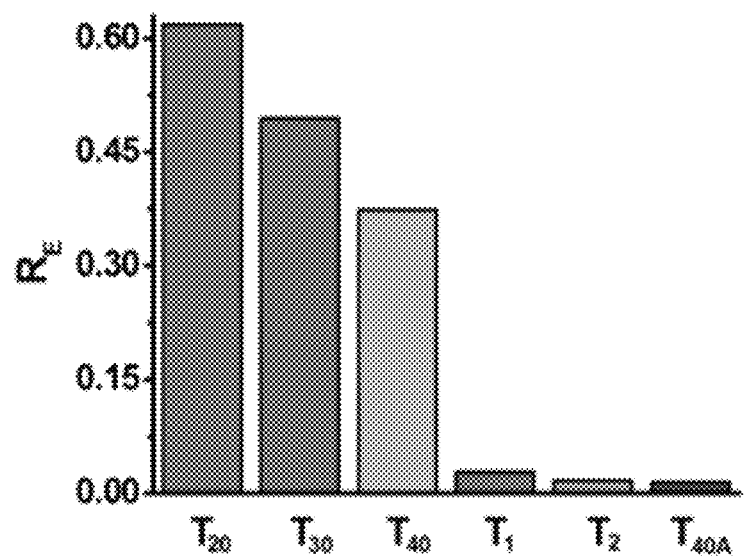
FIGS. 10A, 10B, 10C, and 10D show the fluorescence recovery of P-DNA@1 (50 nM/45 µM) or P-DNA@2 (50 nM/40 µM) systems by target $T_{20}$, $T_{30}$, $T_{40}$, $T_1$, $T_2$ and $T_{40A}$ at the fixed concentration of 50 nM or at varying concentrations.
Figure 10B:
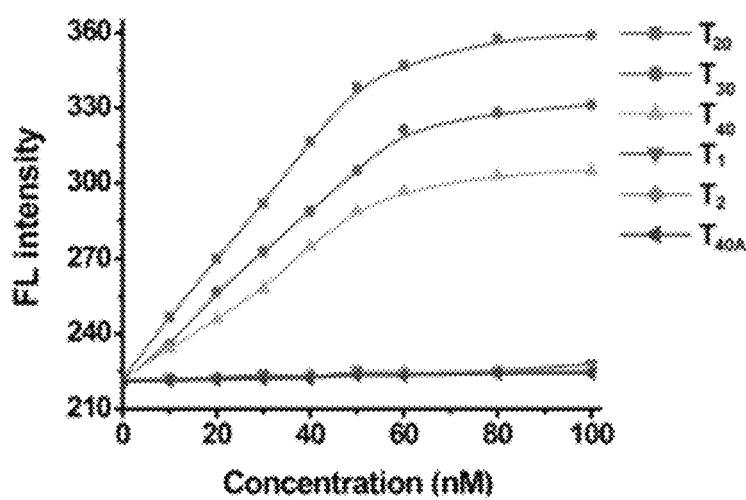
Figure 10C:
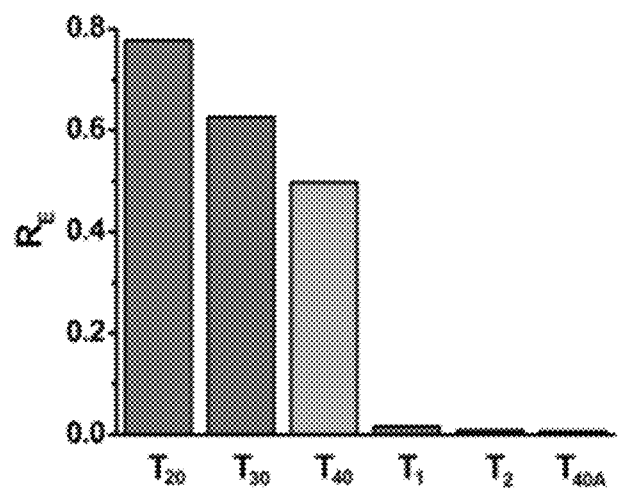
Figure 10D:
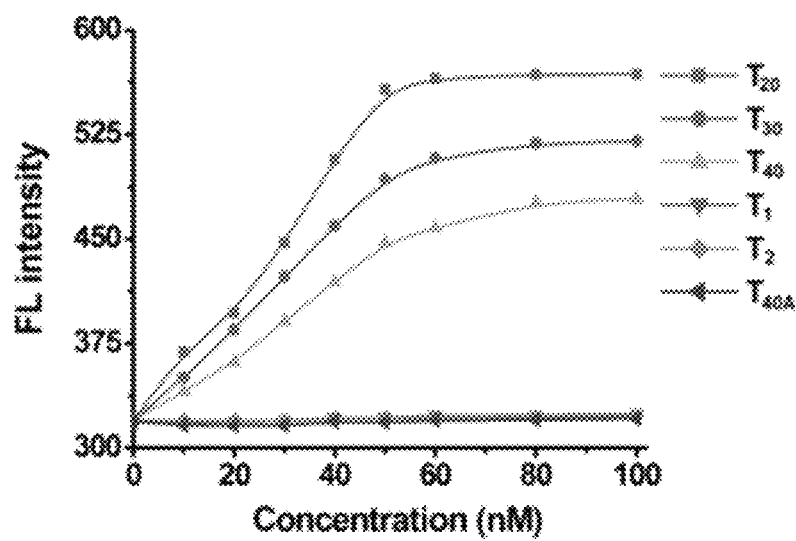
Figure 11A:
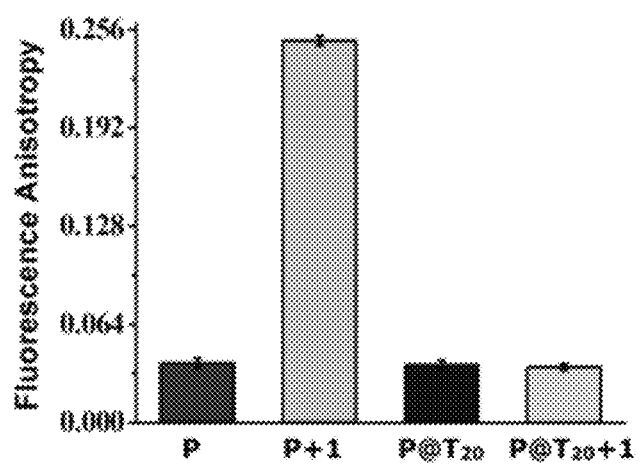
FIGS. 11A and 11B show the fluorescence anisotropy changes of P-DNA (P) P-DNA@$T_{20}$ (P@$T_{20}$, 50 nM/50 nM) before and after the addition of compound 1 (45 µM) or 2 (40 µM).
Figure 11B:
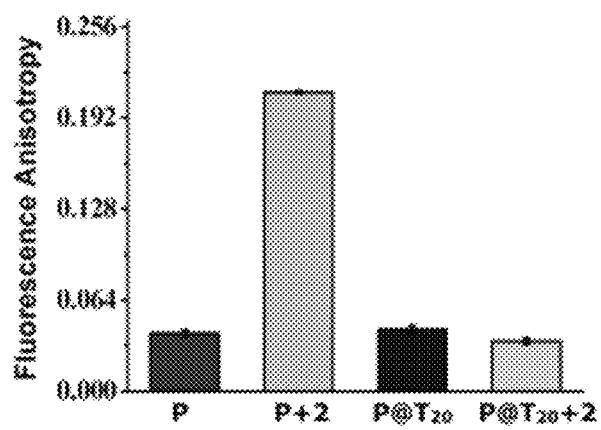
Figure 12A:
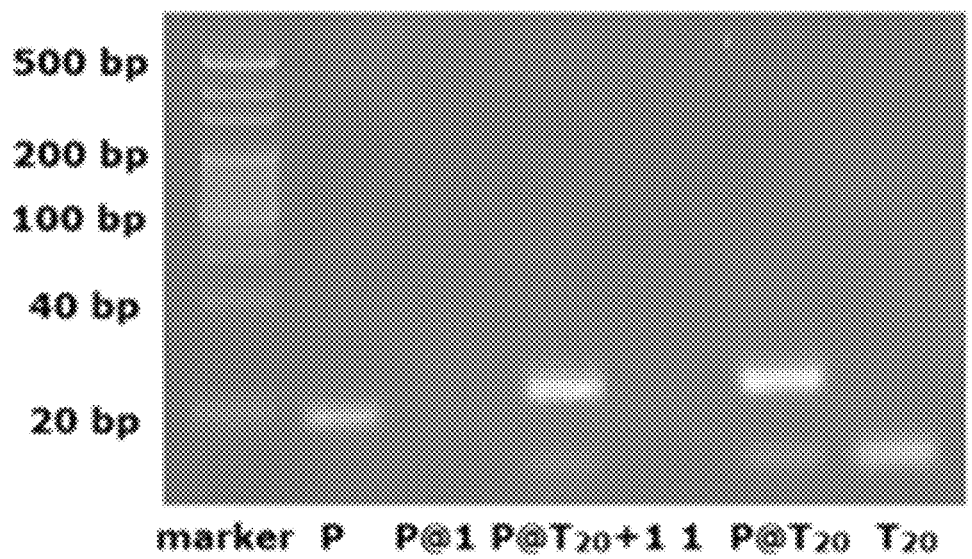
FIGS. 12A and 12B refer to a gel electrophoresis of P-DNA (P, 50 nM), P-DNA@$T_{20}$ (P@$T_{20}$, 50 nM/50 nM) before and after the addition of compound 1 (45 µM) or 2 (40 µM).
Figure 12B:
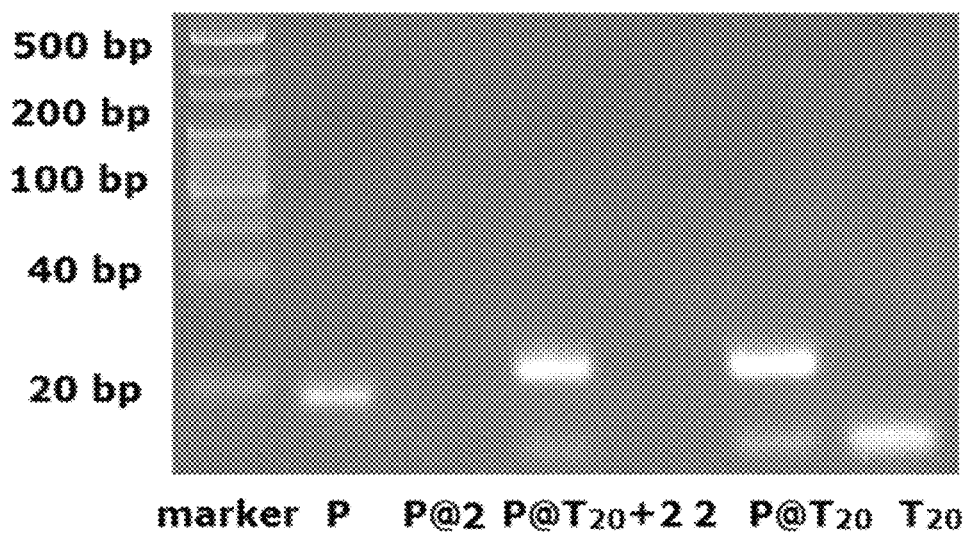

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. The expression that a material "is" a certain element as used herein such as that a solvent is water or the like means that the material essentially consists of said element. As used herein, the forms "a," "an," and "the," are intended to include the singular and plural forms unless the context clearly indicates otherwise.

The present invention provides a method of preparing a crystalline lanthanum-carboxylate coordination polymer.

Said term "lanthanum-carboxylate coordination polymer" refers to a compound comprising and in particular essentially consisting of repeating lanthanum-carboxylate coordination entities. A "coordination entity" possesses a lanthanum ion bound to other atoms or groups of components referenced as ligands. The term "ligands" refers to the components with groups or atoms bound to the lanthanum ion, thereby the lanthanum ion usually occupies a central position in said coordination entity. The term "carboxylate" as used herein indicates that the ligands have one or more carboxylic acid moieties and are preferably bound to the lanthanum ion through one or more of their carboxylic acid moieties.

Preferably, the crystalline lanthanum-carboxylate coordination polymer comprises and in particular essentially consists of repeating coordination entities extending in two dimensions forming a 2D coordination structure, i.e. the coordination polymer comprises and in particular is a 2D coordination polymer, or extending in three dimensions forming a 3D structure, i.e. the coordination polymer comprises and in particular is a 3D coordination polymer.

The expression "essentially consisting of" in relation to the crystalline lanthanum-carboxylate coordination polymer does not exclude that further ions such as $NO_3^-$ ions from the preparation process or water molecules are still present in the coordination polymer.

The lanthanum-carboxylate coordination polymer prepared according to the method of the present invention is crystalline, which shall mean that the atoms or molecules are substantially organized in a structure known as a crystal. Said term is generally used in the art for any structure of ions, molecules, or atoms that are held together in an ordered arrangement. A crystalline structure is one of two types of structural ordering of atoms, ions or molecules the other being the amorphous structure which is irregular and lacks an orderly arrangement of structural units. Whether a compound is crystalline and the respective crystal system can, for example, be confirmed by means of X-ray diffraction. Preferably, the crystalline lanthanum-carboxylate coordination polymer comprises and in particular essentially consists of crystals possessing monoclinic or hexagonal space groups.

The method of the present invention comprises steps of:
(i) preparing a mixture comprising lanthanum ions and a pyridyl ligand which pyridyl ligand is a quaternized carboxylate pyridyl ligand and optionally subjecting the mixture to conditions under which a precipitate is formed and separating the precipitate;
(ii) subjecting the mixture of step (i) or the precipitate of step (i) to conditions under which crystals of the lanthanum-carboxylate coordination polymer are formed;
(iii) separating the crystals of the lanthanum-carboxylate coordination polymer from the mixture.

The lanthanum in the crystalline lanthanum-carboxylate coordination polymer is preferably of the oxidation state +3.

The feature that the mixture comprises the pyridyl ligand as used herein is to be understood to cover any protonated or deprotonated form of said pyridyl ligand due to the presence of further components in the mixture added, for example, for dissolving it.

The term "pyridyl ligand" as used herein generally refers to a ligand comprising at least one optionally substituted pyridine ring.

The pyridyl ligand is a pyridyl ligand which has one or more carboxylic acid moieties, which means herein one or more free carboxylic acid functions. More preferably, the pyridyl ligand is a pyridyl ligand which has two or more and in particular which has three carboxylic acid moieties, i.e. three free carboxylic acid functions.

The one or more, in particular three, carboxylic acid moieties are directly or indirectly attached to the at least one pyridine ring. The term "quaternized" as used herein means that the pyridyl ligand has at least one quaternary ammonium salt group, i.e. at least one positively charged moiety comprising a nitrogen atom, which nitrogen atom binds to carbon atoms via four covalent bonds. In particular, the pyridyl ligand is a zwitterionic quaternized carboxylate pyridyl ligand, i.e. is a molecule with both positive and negative charges.

The first pyridyl ligand preferably has a structure of Formula (I):

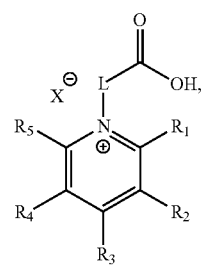

Formula (I)

wherein X is a halogen, in particular selected from Cl, Br or I and most preferably Br. Two of $R^1$ to $R^5$ area group of Formula (II):

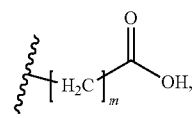

Formula (II)

m is an integer and selected from 0, 1 or 2, in particular m is selected from 0 or 1 and most preferably m is 0, e. the carboxylic acid moieties are directly attached to carbon atoms of the pyridine ring. The other of $R^1$ to $R^5$ are hydrogen. Preferably, $R^2$ and $R^4$ are a group of Formula (II) each and $R^1$, $R^3$ and $R^5$ are hydrogen.

L is a linking group selected from an alkyl group, an aralkyl group, an alkaryl group, an alkarylalkyl group or an aryl.

The term "alkyl group" as used herein refers to saturated, straight-chain or branched hydrocarbons which may, for example, contain between 1 and 20 carbon atoms such as 1 to $$\{\!\!\{\!-\!CH_2\!\!-\!\!\}_n\!\!\}$$

5 carbon atoms. In particular, the alkyl group has a structure of with n being an integer and selected from 0, 1, 2 or 3.

An "aralkyl group" means an aryl with an alkyl substituent, and the term 'alkaryl' refers to an alkyl group with an aryl as substituent. An "alkarylalkyl" group means an alkyl group substituted with an aryl which aryl is substituted with an alkyl.

The term "aryl" as used herein, refers to an aromatic mono- or polycyclic ring system, of which all the ring atoms are carbon, and which ring system has a maximum number of double bonds, in particular a delocalized, conjugated 7-electron system. A preferred aryl is benzene (or phenyl).

L is preferably selected from

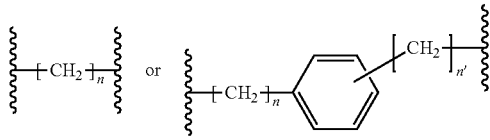

with n and n' being an integer and independently selected from 0, 1, 2 or 3.

Further preferred, L is selected from

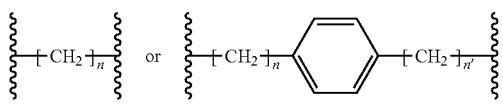

with n and n' being an integer and independently selected from 0, 1, 2 or 3. n is more preferably selected from 1 or 2, in particular it is 1. n' is more preferably selected from 0 or 1 and is in particular 0, i.e. the carboxylic acid moiety is directly attached to the benzene ring.

L is most preferably selected from

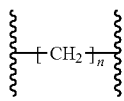

with n being 1 or

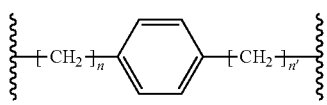

with n being 1 and n' being 0.

The pyridyl ligand has more preferably a structure of Formula (III):

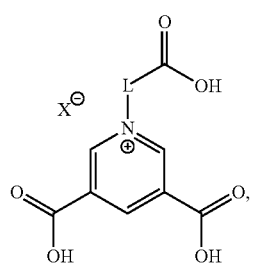

Formula (III)

with X and L being as defined above.

In particular embodiments of the present invention, the pyridyl ligand has a structure of Formula (IV):

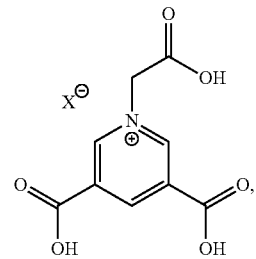

Formula (IV)

with X being as defined as above, in particular being Br.

In alternative embodiments of the present invention, the pyridyl ligand has a structure of Formula (V):

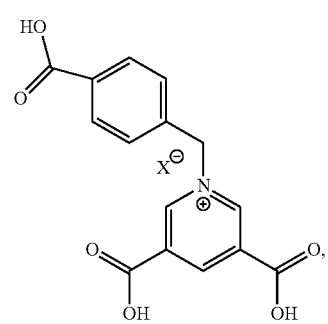

Formula (V)

with X being as defined as above, in particular being Br.

Step (i) preferably comprises steps of:
a) preparing a first pre-mixture comprising mixing the pyridyl ligand and a solvent;
b) preparing a second pre-mixture comprising mixing a lanthanum salt and a solvent;
c) adding the second pre-mixture to the first pre-mixture.

The pyridyl ligand can be in form of a powder.

The solvent in step a) and step b) preferably comprises an aliphatic alcohol, water or a mixture of both. The term "aliphatic alcohol" as used herein means an aliphatic hydrocarbon, preferably a branched or straight chain alkane, wherein at least one hydrogen atom of the aliphatic hydrocarbon is substituted with a hydroxyl group, preferably one hydrogen atom is substituted with a hydroxyl group referenced as monohydric aliphatic alcohol. More preferably, the aliphatic alcohol is a monohydric aliphatic alcohol, still more preferably a monohydric alcohol with 1 to 3 carbon atoms, further preferably with 1 to 2 carbon atoms. More preferably, the aliphatic alcohol is methanol. The solvent in step a) and step b) most preferably essentially consists of methanol or water.

Step a) preferably further comprises a step of adjusting the pH to a pH of between about 5 and about 7, more preferably to a pH of about 6. The pH is preferably adjusted by adding a base. The base is preferably an alkali hydroxide. Alkali hydroxides are a class of chemical compounds which are composed of an alkali metal cation, i.e. one of lithium (Li), sodium (Na), potassium (K), rubidium (Rb), caesium (Cs), and the hydroxide anion (HO—). In particular, the alkali metal cation is K or Na. More preferably, the base is NaOH, i.e. sodium hydroxide such as 0.1 M NaOH. In such embodiments, the first pre-mixture comprises the pyridyl ligand, the solvent of step a) and NaOH.

The lanthanum salt is preferably a salt of lanthanum of the oxidation state +3, in particular it is a hydrate of $La(NO_3)_3$, in particular the hexahydrate. Thus, the lanthanum salt is most preferably $La(NO_3)_3 \times 6\ H_2O$.

In especially preferred embodiments, both solvents in step a) and step b) essentially consist of methanol or water.

The first pre-mixture can be prepared by suspending the pyridyl ligand in the solvent or by dissolving it in the solvent. The pyridyl ligand in step a) is preferably used in a molar ratio compared to the lanthanum salt in step b) of more than about 1:1 to about 2:1, in particular of about 1.5:1.

The mixture prepared in step (i) is preferably a solution, i.e. a homogeneous mixture comprising the lanthanum ions and the pyridyl ligand in the solvents from step a) and b) and optionally the base.

In preferred embodiments of the present invention, the method comprises steps of:

(i) preparing a mixture comprising lanthanum ions and a pyridyl ligand which pyridyl ligand is a quaternized carboxylate pyridyl ligand and subjecting the mixture to conditions under which a precipitate is formed and separating the precipitate;

(ii) subjecting the precipitate of step (i) to conditions under which crystals of the lanthanum-carboxylate coordination polymer are formed;

(iii) separating the crystals of the lanthanum-carboxylate coordination polymer from the mixture.

Step (i) in such embodiments preferably comprises steps of:

a) preparing a first pre-mixture comprising mixing the pyridyl ligand which preferably has a structure of Formula (IV):

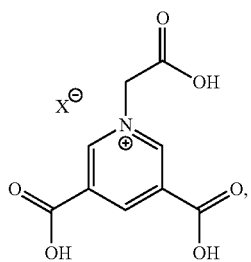

Formula (IV)

with X as defined above, preferably X is Br, and a solvent which preferably essentially consists of methanol; in particular further comprising a step of adjusting the pH to a pH of about 6 by adding NaOH such as 0.1 M NaOH;

b) preparing a second pre-mixture comprising mixing a lanthanum salt which is preferably $La(NO_3)_3 \times 6\ H_2O$ and a solvent, which preferably essentially consists of methanol;

c) adding the second pre-mixture to the first pre-mixture;

d) subjecting the mixture to conditions under which a precipitate is formed and separating the precipitate.

Step d) in particular further comprises stirring the mixture after step c) for between about 15 min and about 60 min, in particular for about 30 min, for forming the precipitate and separating the precipitate preferably by filtration. Preferably, step d) further comprises a step of purifying the precipitate in particular by washing with a washing solvent comprising an aliphatic alcohol, most preferably the washing solvent essentially consists of methanol.

Step (ii) in such embodiments preferably comprises steps of:

a) adding a solvent, which solvent preferably comprises and in particular essentially consists of water to the precipitate at a temperature of between about 20° C. and about 30° C., in particular at a temperature of about 25±2° C.;

b) allowing the mixture after step a) to stand at a temperature between about 20° C. and about 30° C., in particular at a temperature of 25±2° C., for at least about 72 hours and most preferably for about 14 days for forming crystals of the lanthanum-carboxylate coordination polymer.

In alternative preferred embodiments of the present invention, the method comprises steps of:

(i) preparing a mixture comprising lanthanum ions and a pyridyl ligand which pyridyl ligand is a quaternized carboxylate pyridyl ligand;

(ii) subjecting the mixture of step (i) to conditions under which crystals of the lanthanum-carboxylate coordination polymer are formed;

(iii) separating the crystals of the lanthanum-carboxylate coordination polymer from the mixture;

wherein step (i) preferably comprises steps of:

a) preparing a first pre-mixture comprising mixing the pyridyl ligand which preferably has a structure of Formula (V):

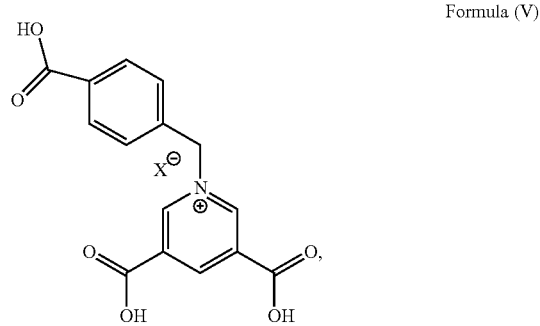

Formula (V)

with X as defined above, preferably X is Br, and a solvent which preferably essentially consists of water; in particular further comprising a step of adjusting the pH to a pH of about 6 by adding NaOH such as 0.1 M NaOH;

b) preparing a second pre-mixture comprising mixing a lanthanum salt which is preferably $La(NO_3)_3 \times 6\ H_2O$ and a solvent, which preferably essentially consists of water;

c) adding the second pre-mixture to the first pre-mixture.

Step (ii) preferably comprises steps of:

a) stirring the mixture at a temperature of at least about 80° C., further preferred at about 100° C. for about 15 min to about 60 min, further preferred for about 30 min;

b) filtering the mixture for obtaining a filtrate and a residue;

c) allowing the filtrate to stand at a temperature of between 20° C. and 30° C., further preferred at a temperature of about 25±2° C., for at least about 72 hours, further preferred for at least about 20 days and in particular for about 28 days to about 31 days for forming crystals of the lanthanum-carboxylate coordination polymer.

The method of the present invention further comprises a step (iii) of separating the crystals of the lanthanum-carboxylate coordination polymer. Said step (iii) preferably comprises steps of:

a) separating the crystals from the mixture;

b) purifying the crystals;

c) drying the crystals, preferably by drying the crystals in vacuo.

Preferably, purifying the crystals in step b) comprises and in particular is carried out by means of washing the crystals with a washing solvent. The washing solvent preferably comprises an aliphatic alcohol, in particular a monohydric alcohol, more preferably a monohydric alcohol with 1 to 3 carbon atoms, most preferably methanol. In particular embodiments of the present invention, the washing solvent essentially consists of methanol.

The present invention in particular encompasses the following preferred embodiments A and B of the method of the present invention:

Embodiment A: The first pyridyl ligand used in step (i) is of Formula (IV):

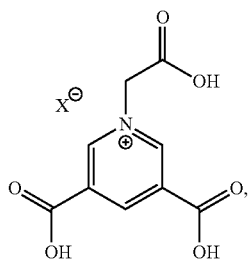

Formula (IV)

with X being Br, i.e. is N-carboxymethyl-3,5-dicarboxyl-pyridinium bromide (H$_3$CmdcpBr) and the lanthanum salt is La(NO$_3$)$_3$×6 H$_2$O, wherein the pyridyl ligand is used in a molar ratio to the lanthanum salt of about 1.5:1. In such embodiment, the crystalline lanthanum-carboxylate coordination polymer preferably comprises and in particular essentially consists of repeating coordination entities extending in three dimensions, i.e. is a 3D coordination polymer, preferably comprising and in particular essentially consisting of asymmetric units with the formula [La$_4$(Cmdcp)$_6$(H$_2$O)$_9$], i.e. which crystalline lanthanum-carboxylate coordination polymer can in embodiments be described as {[La$_4$(Cmdcp)$_6$ (H$_2$O)$_9$]}$_n$ (also referenced as compound 1). As used herein, "asymmetric unit" means the minimal set of atomic coordinates that can be used to generate the entire repetition in a crystal.

Embodiment B: The first pyridyl ligand used in step (i) is of Formula (V):

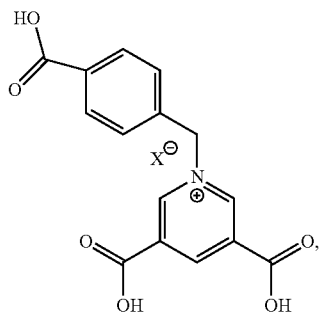

Formula (V)

with X being Br, i.e. is N-(4-carboxybenzyl)-3,5-dicarboxyl-pyridinium bromide (H$_3$CbdcpBr) and the lanthanum salt is La(NO$_3$)$_3$×6 H$_2$O, wherein the pyridyl ligand is used in a molar ratio to the lanthanum salt of about 1.5:1. In such embodiment, the crystalline lanthanum-carboxylate coordination polymer preferably comprises and in particular essentially consists of repeating coordination entities extending in two dimensions, i.e. is a 2D coordination polymer, preferably comprising and in particular essentially consisting of asymmetric units with the formula [La$_2$(Cbdcp)$_3$(H$_2$O)$_{10}$], i.e. which crystalline lanthanum-carboxylate coordination polymer can in embodiments be described as {[La$_2$(Cbdcp)$_3$(H$_2$O)$_{10}$]}$_n$ (also referenced as compound 2).

The present invention further provides a crystalline lanthanum-carboxylate coordination polymer obtained or obtainable by the method described above. In one embodiment of the present invention, the present invention provides a lanthanum-carboxylate coordination polymer obtained by the method described above. In another embodiment of the present invention, the present invention provides a crystalline lanthanum-carboxylate coordination polymer obtainable by the method described above. The crystalline lanthanum-carboxylate coordination polymer preferably comprises and more preferably essentially consists of crystals with a monoclinic or hexagonal space group.

The crystalline lanthanum-carboxylate coordination polymer in preferred embodiments of the present invention is a coordination polymer extending through repeating coordination entities in two or three dimensions, i.e. more preferably is a 2D or 3D coordination polymer.

The crystalline lanthanum-carboxylate coordination polymer is in preferred embodiments obtained or obtainable by the method described above in which the first pyridyl ligand in step (i) has a structure of Formula (IV):

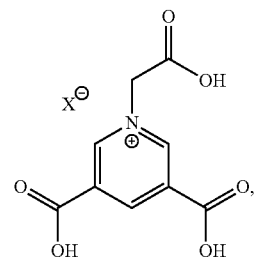

Formula (IV)

with X being Br, which crystalline lanthanum-carboxylate coordination polymer is according to embodiment A above and can be described by the formula {[La$_4$(Cmdcp)$_6$(H$_2$O)$_9$]}$_n$, i.e. is compound 1.

The crystalline lanthanum-carboxylate coordination polymer is in alternative preferred embodiments obtained or obtainable by the method described above in which the first pyridyl ligand in step (i) has a structure of Formula (V):

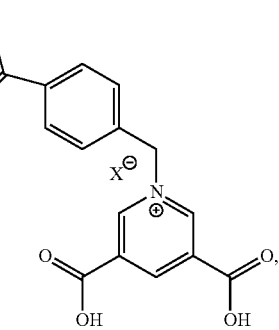

Formula (V)

with X being Br, which crystalline lanthanum-carboxylate coordination polymer is according to embodiment B described above and can be described by the formula $\{[La_2(Cbdcp)_3(H_2O)_{10}]\}_n$, i.e. is compound 2.

The present invention in a third aspect provides a method of detecting a target nucleic acid sequence in a sample. The sample is from a subject such as a mammal, preferably a human and can comprise, for example, blood.

The method of the present invention of detecting a target nucleic acid sequence in a sample comprises steps of:

(i) preparing a mixture of a crystalline lanthanum-carboxylate coordination polymer obtained or obtainable with the preparation method described above and an oligonucleotide probe having a nucleic acid sequence at least partially complementary to said target nucleic acid sequence and being labeled with a fluorescent;

(ii) incubating the mixture with the sample;

(iii) measuring the fluorescence after step (ii);

(iv) determining the presence and/or amount of the target nucleic acid sequence in the sample based on the fluorescence determined in step (iii).

The crystalline lanthanum-carboxylate coordination polymer used in step (i) is preferably obtained or obtainable by the method described above in which the first pyridyl ligand in step (i) has a structure of Formula (IV):

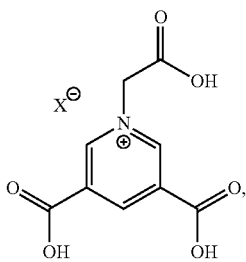

Formula (IV)

which crystalline lanthanum-carboxylate coordination polymer is according to embodiment A above and can be described by the formula $\{[La_4(Cmdcp)_6(H_2O)_9]\}_n$, i.e. is more preferably compound 1.

The crystalline lanthanum-carboxylate coordination polymer used in step (i) is in alternative preferred embodiments obtained or obtainable by the method described above in which the first pyridyl ligand in step (i) has a structure of Formula (V):

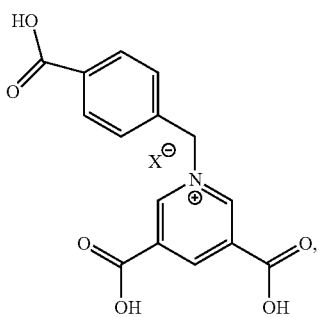

Formula (V)

which crystalline lanthanum-carboxylate coordination polymer is according to embodiment B above and can be described by the formula $\{[La_2(Cbdcp)_3(H_2O)_{10}]\}_n$, i.e. is more preferably compound 2.

The crystalline lanthanum-carboxylate coordination polymer used in step (i) of the method of detecting a target nucleic acid sequence preferably comprises and in particular essentially consists of compound 1, compound 2 or mixtures thereof. Such compounds proved to allow for an exceptional interaction with the oligonucleotide probe and quenching efficiency. The inventors further found that such crystalline lanthanum-carboxylate coordination polymers provide an exceptional quenching efficiency and a particularly high selectivity and specificity with detection limits as low as 112 and 67 pM when using an oligonucleotide probe of SEQ. ID. NO:1 and Sudan virus RNA (SUDV RNA) as target nucleic acid sequence.

The target nucleic acid sequence can be of DNA or RNA, in particular viral RNA such as from Ebolavirus, in particular from Sudan virus such as SUDV RNA comprising or in particular consisting of a sequence having SEQ. ID. NO:2, NO:3 or NO:4, more preferably consisting of SEQ. ID. NO:2. Said part of the SUDV RNA includes nucleotide sequences very specific for the Sudan virus.

The term "oligonucleotide probe" as known in the art refers to a short single-stranded sequence of nucleotides that are synthesized to match a specific region of target DNA or RNA used as a molecular probe to detect said sequence. Said oligonucleotide probe is labeled with a fluorescent, more preferably FAM (fluorescein) is attached to the oligonucleotide probe. The oligonucleotide probe is preferably made up of 10 to 25 nucleotides and more preferably comprises a sequence of SEQ. ID. NO: 1, most preferably it is a FAM-labeled ss-DNA sequence comprising or consisting of SEQ. ID. NO:1.

The incubation in step (ii) of the method of detecting a target nucleic acid sequence may be carried out for at least about 10 min such as by oscillating the mixture.

The wavelength for determining the fluorescence in step (iii) of the method of detecting a target nucleic acid sequence depends on the fluorescent. The skilled person is able to determine the respective absorption and emission wavelength.

Step (iv) of the method of detecting a target nucleic acid sequence may further comprise a step of comparing the fluorescence with at least one reference value such as the fluorescence of a reference sample without the target nucleic acid sequence or at least one reference sample with a predetermined amount of target nucleic acid sequence.

The inventors found that in step (i) the crystalline lanthanum-carboxylate coordination polymer can non-covalently bind to the oligonucleotide probe, in particular strongly absorb the oligonucleotide probe resulting and thereby quench the fluorescence of said oligonucleotide probe via a photo-induced electron transfer process. The oligonucleotide probe in step (ii) can then bind to the target nucleic acid sequence in the sample leading to a fluorescence regeneration.

Hence, the method and the crystalline lanthanum-carboxylate coordination polymer can in particular be used in the diagnosis of Ebolavirus such as Sudan virus infections.

Still further, a kit is provided with the present invention comprising:

(i) a crystalline lanthanum-carboxylate coordination polymer obtained or obtainable with the preparation method described above;

(ii) an oligonucleotide probe having a nucleic acid sequence complementary to a target nucleic acid sequence and being labeled with a fluorescent, in particular a FAM-labeled oligonucleotide probe of SEQ. ID. NO:1.

The crystalline lanthanum-carboxylate coordination polymer in the kit is preferably obtained or obtainable by the preparation method described above in which the first pyridyl ligand in step (i) of the preparation method has a structure of Formula (IV):

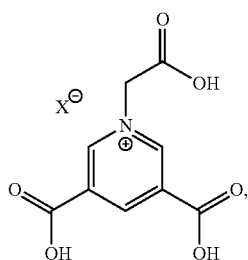

Formula (IV)

which crystalline lanthanum-carboxylate coordination polymer is according to embodiment A above and can be described by the formula $\{[La_4(Cmdcp)_6(H_2O)_9]\}_n$, i.e. is more preferably compound 1.

The crystalline lanthanum-carboxylate coordination polymer in the kit is in alternative preferred embodiments obtained or obtainable by the method described above in which the first pyridyl ligand in step (i) has a structure of Formula (V):

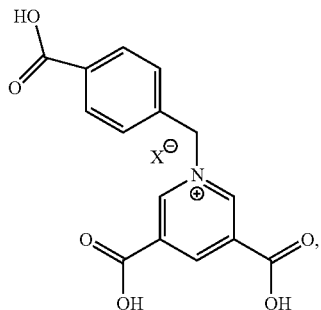

Formula (V)

which crystalline lanthanum-carboxylate coordination polymer is according to embodiment B above and can be described by the formula $\{[La_2(Cbdcp)_3(H_2O)_{10}]\}_n$, i.e. is more preferably compound 2.

In a further aspect, the present invention refers to the use of the crystalline lanthanum-carboxylate coordination polymer obtained or obtainable by the preparation method as described above or the kit in the diagnosis of viral infectious diseases, preferably of Ebolavirus, in particular Sudan virus infections. More specifically, the present invention refers to the use of the crystalline lanthanum-carboxylate coordination polymer or the kit for detecting the presence and/or the amount of a target nucleic acid in a sample from a subject such as a human, in particular Sudan virus RNA preferably comprising or consisting of SEQ. ID. NO:2, NO:3 or NO:4.

EXAMPLE 1

Methods of Preparing Crystalline Lanthanum-Carboxylate Coordination Polymers of the Present Invention

Method of Preparing $\{[La_4(Cmdcp)_6(H_2O)_9]\}_n$ (Compound 1)

Powder of $H_3CmdcpBr$ (45.8 mg, 0.15 mmol) was suspended in methanol (15 mL), and the pH was adjusted to 6.0 with 0.1 M NaOH solution to give clear solution. Then, a solution of $La(NO_3)_3$. $6H_2O$ (43.3 mg, 0.1 mmol) in methanol (1.5 mL) was added and stirred for 30 min. The formed white precipitate was collected by filtration and washed with methanol (5 mL), then re-dissolved in $H_2O$ (30 mL) at room temperature to give a clear colorless solution. After standing at ambient temperature for about two weeks, the needle crystals of compound 1 were formed (44 mg, 86%). Anal. Calcd. for $C_{54}H_{48}N_6O_{45}La_4$. $2H_2O$ (compound $1.2H_2O$): C, 30.98, H, 2.49, N, 4.02. Found: C, 30.85, H, 2.39, N, 3.98%. IR (KBr disc) v 3424 (s), 2355 (w), 1649 (s), 1612 (s), 1384 (s), 1238 (w), 1178 (w), 774 (w), 724 (m), 623 (m), 526 (m).

Method of Preparing $\{[La_2(Cbdcp)_3(H_2O)_{10}]\}_n$ (Compound 2)

A solution of $H_3CbdcpBr$ (114.6 mg, 0.3 mmol) in $H_2O$ (50 mL) was adjusted to pH 6.0 with 0.1 M NaOH solution. Then, a solution of $La(NO_3)_3$. $6H_2O$ (86.6 mg, 0.2 mmol) in $H_2O$ (50 mL) was added. The resulting mixture was stirred at 100° C. for 0.5 h to give a clear solution. The resulting colorless solution was filtered, then cooled to room temperature and allowed to stand for one month to give the block crystals of compound 2 (107 mg, 80%). Anal. Calcd. for $C_{45}H_{47}N_3O_{28}La_2.2H_2O$: C, 38.84, H, 3.69, N, 3.02. Found: C, 39.10, H, 3.54, N, 2.93%. IR (KBr disc) v 3393 (s), 3068 (s), 1649 (s), 1608 (s), 1596 (s), 1542 (s), 1402 (w), 1370 (w), 1226 (w), 1164 (w), 1016 (w), 924 (w), 856 (w), 768 (m), 720 (m).

Compounds 1 and 2 were synthesized in 86% and 80% yields from the reaction of $La(NO_3)_3$. $6H_2O$ with deprotonated pyridinium carboxylate. Compounds 1 and 2 are moisture and water stable. The powder X-ray diffraction (PXRD) pattern of the fresh powder of 1 and 2 immersed in $H_2O$ for 48 h, are in agreement with those of the simulated, indicating theirs bulky phase purity and water stability (FIGS. 1A and 1B). Thermogravimetric analysis (TGA) indicates that the as-synthesized samples of 1 and 2 are stable up to ca. 300° C. (FIG. 1C).

EXAMPLE 2

X-Ray Crystal Structure Determinations of the Obtained Crystalline Lanthanum-Carboxylate Coordination Polymers Crystallographic measurement was made on a Bruker APEX II diffractometer by using graphite-monochromated Mo Kα (λ=0.71073 Å) irradiation for compounds 1 and 2. The data were corrected for Lorentz and polarization effects with the SMART suite of programs and for absorption effects with SADABS (Sheldrick G M. SADABS, program for empirical absorption correction of area detector data. University of Göttingen, Germany, 1996). The structure was solved by direct methods and refined on $F^2$ by full-matrix least-squares techniques with SHELXTL-97 program (Sheldrick G M. SHELXS-97 and SHELXL-97, Programs for the Solution and Refinement of Crystal Structures. University of Göttingen, Germany, 1997). In compound 1, the location of the hydrogen atoms on the coordinated waters were suggested by Calc-OH program in WinGX suite, their O—H distances were further restrained to O—H=0.85 Å and thermal parameters constrained to $U_{iso}(H)=1.2U_{eq}(O)$ (Farrugia, L. J., J. Appl. Crystallogr., 1999, 32, 837). While for compound 2, the hydrogen atoms on the coordinated water solvates were not located. In both 1 and 2, a large amount of spatially delocalized electron density in the lattice was found but acceptable refinement results could not be obtained for this electron density. The solvent contribution was then modeled using SQUEEZE in the Platon program suite (Spek, A. L., J. Appl. Crystallogr., 2003, 36, 7). Crystallographic data have been deposited with the Cambridge Crystallographic Data Center as supplementary publication numbers 1486699 and 1486700. A summary of the key crystallographic data for 1 and 2 is given in Table 1.

TABLE 1

Crystallographic data for compounds 1 and 2

| compounds | 1 | 2 |
|---|---|---|
| Molecular formula | $C_{54}H_{48}N_6O_{45}La_4$ | $C_{45}H_{27}N_3O_{28}La_2$ |
| Formula weight | 2056.62 | 1335.52 |
| Crystal system | hexagonal | monoclinic |
| Space group | P-31c | C2/c |
| a (Å) | 14.9964 (13) | 16.6409 (16) |
| b (Å) | 14.9964 (13) | 21.445 (2) |
| c (Å) | 23.100 (2) | 37.803 (4) |
| α (°) | 90.00 | 90.00 |
| β (°) | 90.00 | 21.445 (2) |
| γ (°) | 120.00 | 90.00 |
| V ($Å^3$) | 4499.0 (7) | 13297 (2) |
| Z | 2 | 8 |
| T/K | 296 (2) | 153 (2) |
| $D_{calc}$ (g · cm) | 1.518 | 1.163 |
| λ (Mo-Kα) | 0.71073 | 0.71073 |
| μ ($cm^{-1}$) | 1.948 | 0.892 |
| Total reflections | 50116 | 65088 |
| Unique reflections | 50116 | 17489 |
| No. observations | 43659 | 16940 |
| No. parameters | 163 | 866 |
| $R^a$ | 0.0404 | 0.0390 |
| $wR^b$ | 0.1063 | 0.1002 |
| $GOF^c$ | 1.043 | 1.029 |
| $\Delta\rho_{max}$ (e $Å^{-3}$) | 2.221 | 0.665 |
| $\Delta\rho_{min}$ (e $Å^{-3}$) | −2.943 | −0.374 |

$^aR_1 = \Sigma||F_o| - |F_c||/\Sigma|F_o|$.
$^bwR_2 = \{\Sigma[w(F_o^2 - F_c^2)^2]/\Sigma[w(F_o^2)^2]\}^{1/2}$.
$^cGOF = \{\Sigma[w(F_o^2 - F_c^2)^2]/(n - p)\}^{1/2}$, where n is the number of reflections and p is total number of parameters refined Crystal Structure of $\{[La_4(Cmdcp)_6(H_2O)_9]\}_n$ (Compound 1)

Compound 1 crystallizes in hexagonal space group $P3_1c$ and its asymmetric unit contains one Cmdcp ligand, two coordinated water molecules and three individual La atoms, in which La1 and La3 atoms are located at the center of hexagonal axis, while La2 at triad axis. As shown in FIG. 2A to 2D, La1 and La3 are nine-coordinated while La2 has a rare coordination number of twelve. Among these three La ions, La1 (FIG. 2A) and La3 are associated by nine oxygen atoms from six monodentate methyl carboxylate of six different Cmdcp ligands and three water molecules, thereby forming a monocapped square-antiprism coordination geometry (FIG. 2B). The coordination number of La2 is fulfilled by six chelating benzylcarboxylates of six different Cmdcp ligands (FIG. 2C), thereby giving an icosahedron coordination geometry (FIG. 2D).

In compound 1, the Cmdcp ligand in the asymmetric unit is coordinated to four La atoms through two monodentate carboxylate groups, and one chelating meanwhile acting as μ-carboxylate group. Each La atom extends to other eleven La atoms through six Cmdcp ligands in three directions, thereby forming 3D channels. It's worth mentioning that the edges of the channels are decorated with quaternary ammonium groups from ligands as shown in blue in FIG. 3B.

The 3D supramolecular structure possesses large circular channels that are occupied with guest water molecules. The guest molecules were highly disordered in the channel and hence, the SQUEEZE was applied to refine the guest-free structure (Spek, A. L., Acta. Crystallogr. D. Biol. Crystallogr., 2009, 65, 148). The approximate diameter of the circular channel, calculated considering the van der Waals surface, is 15.0 Å. The potential solvent-accessible void in guest-free turns out to be 1421 Å, which is 32% of the unit cell volume (Spek, A. L., J. Appl. Crystallogr., 2003, 36, 7).

Crystal Structure of $\{[La_2(Cbdcp)_3(H_2O)_{10}]\}_n$ (Compound 2)

Compound 2 crystallizes in monoclinic space group C2/c and the asymmetric unit consists of one $[La_2(Cbdcp)_3(H_2O)_{10}]$ molecule. The La centers are linked by a pair of μ-COO groups and a single μ-COO group alternatively in a —[double—single]$_n$— chain fashion (FIG. 4). Each La center is further coordinated to one monodentate carboxylate from one Cbdcp ligand. The other carboxylate of this Cbdcp ligand is connected to the neighboring chain as the single μ-COO group, thereby forming a 2D structure in the ac plane (FIG. 5). The remaining carboxylates are free and deprotonated to balance the positive charge of the pyridinum cations and La(III) centers. In compound 2, each La(III) has a monocapped square-antiprism coordination geometry with the coordination of nine oxygen atoms from three μ-COO carboxylate groups, one monodentate carboxylate groups and five water molecules.

EXAMPLE 3

Sensing Properties of Compounds 1 and 2 Towards Sudan Virus RNA

General Procedures

IR spectra were recorded on a Nicolet MagNa-IR 550 infrared spectrometer. Elemental analyses for C, H, and N were performed on an EA1110 CHNS elemental analyzer. Thermogravimetric analysis (TGA) was performed on a SDTA851 thermogravimetric analyzer at a heating rate of 10° C. $min^{-1}$ under a nitrogen gas flow in an $Al_2O_3$ pan. Powder X-ray diffraction (PXRD) spectra were recorded with a Rigaku D/max-2200/PC. The X-ray generated from a sealed Cu tube was mono-chromated by a graphite crystal and collimated by a 0.5 mm MONOCAP (λCu—Kα=1.54178 Å). The tube voltage and current were 40 kV and 40 mA, respectively. Fluorescence spectra and fluorescence anisotropy were measured on an LS55 spectrofluorimeter. Zeta potential measurement was carried out on a NanoZS90 zetasizer.

The DNA sequences were purchased from Sangon Inc. (Shanghai, China) and the RNA sequences were purchased from TaKaRa. (Dalian, China). The sequences are given in Table 2.

All the samples were dissolved in 100 μM Tris-HCl buffer solution (pH 7.4, 100 mM NaCl, 5 mM MgCl$_2$). DNA was stored at 4° C. and RNA was stored at −80° C. for use. The ligands of H$_3$CmdcpBr and H$_3$CbdcpBr were synthesized according to the known method (Chen, M. et al., Dalton. Trans., 2015, 44, 13369; Chen, J. X. et al., Inorg. Chem., 2014, 53, 7446). All the other reagents and solvents were obtained from commercial sources and used without further purification. All the instruments used for the detection of Sudan virus RNA sequences were sterilized in an autoclavable container.

TABLE 2

DNA and RNA sequences used in the present invention

| | comprises SEQ. ID. NO. | Sequence |
|---|---|---|
| oligonucleotide probe/probe DNA (P-DNA) | FAM-labeled SEQ. ID. NO: 1 | FAM-5'-TTAAAAAGTTTGTCCTCATC-3' |
| Complementary target SUDV RNAs $T_{20}$ $T_{30}$ $T_{40}$ | SEQ. ID. NO: 2 SEQ. ID. NO: 3 SEQ. ID. NO: 4 | 5'-GAUGAGGACAAACUUUUUAA-3' 5'-UCUUCCGUUUGAUGAGGACAAACUUUUUAA-3' 5'-AUGAUGGUGAUCUUCCGUUUGAUGAGGACAAACUUUUUAA-3' |
| One base pair mutated for complementary target RNA ($T_1$) | SEQ. ID. NO: 5 | 5'-GAUGAGGACACACUUUUUAA-3' |
| Scrambled non-specific RNA ($T_2$) | SEQ. ID. NO: 6 | 5'-GGCAAUCAGCUGGACACAUG-3' |

Sudan Virus RNA Sequence Detection Experiments

The fluorescence measurements were performed at room temperature with both excitation and emission slit width 10.0 nm. The fluorescence intensity at 518 nm with excitation at 480 nm was used for quantitative analysis.

Firstly, fluorescence quenching experiments of probe DNA (P-DNA) by compounds 1, 2, $H_3$CmdcpBr, $H_3$CbdcpBr and $La(NO_3)_3$ were performed by keeping the concentrations of P-DNA constant, while gradually increasing the concentrations of each compound.

Specifically, to a solution of P-DNA (50 nM) in 100 μM Tris-HCl (pH 7.4, 100 mM NaCl, 5 mM $MgCl_2$) were added aliquots of a solution of each compound containing P-DNA (50 nM) in the same buffer and oscillated. The corresponding fluorescence spectra were measured until saturation was observed. The quenching efficiency ($Q_E$%) was calculated according to Eq. (1).

$$Q_E\%=(1-F_M/F_0)\times 100\% \quad (1)$$

wherein $F_M$ and $F_0$ are fluorescence intensities at 518 nm in the presence and absence of each compound, respectively.

Secondly, fluorescence recovery experiments were conducted at room temperature by adding target SUDV RNA sequences of varying concentrations to the above saturated P-DNA@compound solution. The oscillation time was 30 min for P-DNA@1 and 18 min for P-DNA@2 until saturation of fluorescence recovery was observed. Fluorescence recovery efficiency was calculated according to Eq. (2).

$$R_E=F_T/F_M-1 \quad (2)$$

wherein $F_T$ and $F_M$ are the fluorescence intensities at 518 nm in the presence and the absence of target RNA, respectively.

Sensing Properties of Compounds 1 and 2

As discussed above, with cationic metal centers and the conjugated 7-electrons in compounds 1 or 2, they can interact with aromatic nucleotide bases in the FAM-labeled, negatively charged P-DNA (on-state) to quench the FAM fluorescence (off-state) via photoinduced electron transfer (PET) (Daly, B. et al., Chem. Soc. Rev., 2015, 44, 4203; Atchison, J. et al., Chem. Commun., 2015, 51, 16832). The interactions of compounds 1 and 2 with FAM-labeled SEQ. ID. NO: 1, a complementary sequence of SUDV RNA, have further been evaluated. As shown in FIG. 6, the quenching efficiency of 1 and 2 are 70% and 57%, with saturated concentrations of 45 μM and 40 μM, respectively. Thus, both compounds 1 and 2 can quench the photoluminescence of the P-DNA due to the formation of P-DNA@1 or P-DNA@2 systems, i.e. P-DNA interacts with compounds 1 or 2 referenced herein as "P-DNA@1" or "P-DNA@2" systems. The results show that compound 1 has a higher quenching efficiency than compound 2. The inventors assume that this might be due to the exposure of positively charged quaternary ammonium centers at the edge of the channels of compound 1 that provide stronger electrostatic interaction with P-DNA. To verify such hypothesis, the binding affinity of compounds 1 and 2 has been calculated toward P-DNA. The binding constant is calculated via the following double logarithm Eq. (3) wherein $F_o$ and F are the fluorescence intensities at 518 nm in the absence and presence of MOF, $K_b$ is the binding constant and n is the number of binding sites (Zhang, G. W. et al., Spectrochim. Acta. A. Mol. Biomol. Spectrosc., 2010, 76, 410). The binding constants between compounds 1 or 2 and P-DNA are $3.0\times10^4$ $M^{-1}$ and $1.5\times10^4$ $M^{-1}$, respectively, which are in coincidence with their quenching efficiency.

To further explore the key contributing factors that cause the fluorescence quenching, the quenching efficiency of each individual component has been analyzed ($H_3$CbdcpBr, $H_3$CmdcpBr and $La(NO_3)_3$) at varying concentrations. As shown in FIG. 7A to 7B, the quenching efficiency of $La(NO_3)_3$, $H_3$CbdcpBr and $H_3$CmdcpBr are 79.8%, 8.3% and 7.5% with saturated concentrations of 60 μM, 30 μM and 30 μM, indicating that La$^{3+}$ ion plays a major factor in the quenching process.

$$\log(F_0-F)/F = n \log[\text{compound}] + \log K_b \quad (3)$$

In the P-DNA@1 or P-DNA@2 systems, addition of the relevant complementary target SUDV RNA sequences leads to stable DNA/RNA hybrid duplexes (Rauzan, B. et al., Biochemistry, 2013, 52, 765). The formation of hybrid duplex structures would keep the P-DNA away from the surface of compounds 1 and 2, leading to the fluorescence regeneration (on state). Thus, the sensing capability of P-DNA@1 and P-DNA@2 systems for SUDV RNA sequences was evaluated by the fluorescence regeneration induced by the addition of complementary SUDV RNA sequences ($T_{20}$). The fluorescence intensity recovery was found to be time dependent. The fluorescence intensity increased with incubation time and remained unchanged when the incubation time was longer than 30 min for P-DNA@1 and 18 min for P-DNA@2 (FIGS. 8A and 8B) with lowest concentration of 25 nM of $T_{20}$ for both systems. The longer recovery time of P-DNA@1 compared to that of P-DNA@2 is probably due to adsorption of the P-DNA by the pores of compound 1 which shields its re-combination with target RNA, and makes the hybridization more difficult. While for P-DNA@2, the flat surface of compound 2 lowers the steric hindrance and favors target-probe hybridization. In addition, the increased concentration of target SUDV RNA sequences led to a gradual increase in the fluorescence intensity until saturation was observed at the concentration of 50 nM for both P-DNA@1 and P-DNA@2 (FIGS. 9A and 9B). Under this condition, the fluorescence intensity of P-DNA@1 and P-DNA@2 shows good linear relationships with the concentration of target RNA (inset of FIGS. 9A and 9B) leading to detection limits of 112 μM with RSD of 1.2% and 67 μM with RSD of 1.1%, respectively.

To investigate the specificity of P-DNA@1 and P-DNA@2 toward $T_{20}$, two RNA sequences have been selected, including one base pair mutated RNA $T_1$ (one A base of $T_{20}$ was replaced with C) and non-specific $T_2$ to hybridize with P-DNA in the two systems. As shown in FIG. 10A and FIG. 10C, the introduction of completely complementary target Sudan virus RNA $T_{20}$ results in significant fluorescence enhancement with the recovery efficiency ($R_E$) reaching 0.62 for P-DNA@1 and 0.78 for P-DNA@2. Under the same conditions, the $R_E$ is only 0.03 for $T_1$ and 0.02 for $T_2$ with P-DNA@1 system, 0.02 for $T_1$ and 0.01 for $T_2$ with P-DNA@2 system. In addition, the fluorescence recovery induced by $T_{20}$ shows much higher concentration dependence than that by $T_1$ and $T_2$ (FIG. 10B and FIG. 10D). These results collectively point out that the formed sensing platforms are high selective towards the target SUDV RNA sequences.

Sequence $T_{20}$ is part of the complete Sudan virus genome (GenBank No. AF173836.1) that has 2926 nucleotides in length. Therefore, in order to further evaluate the application of P-DNA@1 or P-DNA@2 in the detection of SUDV RNA sequences, the length of target SUDV RNA sequences has been extended from 20 ($T_{20}$) bases to 30 ($T_{30}$) and 40 ($T_{40}$) bases. As shown in FIG. 10A to 10D, introducing $T_{20}$, $T_{30}$ and $T_{40}$ to both systems results in significant fluorescence enhancement with $R_E$ values being 0.62, 0.49 and 0.37 for P-DNA@1, 0.78, 0.63 and 0.50 for P-DNA@2. Under this condition, the detection limits are 112 pM for $T_{20}$, 806 μM for $T_{30}$ and 1016 pM for $T_{40}$ for the P-DNA@1 system, 67 μM for $T_{20}$, 83 pM for $T_{30}$ and 92 μM for $T_{40}$ for the P-DNA@2 system. These observations suggest that the recovery efficiency decreases as the length of target RNA sequence increases. In addition, using one base-mutated target RNA $T_{40A}$ as interfered RNA sequences for $T_{40}$ gives $R_E$ values as low as 0.01 for both systems.

The above positive results confirm that P-DNA@1 and P-DNA@2 are highly efficient and exceptional selective sensing platforms for SUDV RNA sequences which may be rationalized from the unique structural features of compounds 1 and 2. The zeta potential of compounds 1 and 2 are +3.1 mV and 3.6 mV, indicating that they are positively charged (Hunter R J. Zeta potential in colloid science: principles and applications. Academic press, 2013). With the conjugated 7-electron system in the compounds and aromatic nucleotide bases in the probe DNA, compounds 1 and 2 can absorb P-DNA through electrostatic and 7-stacking interactions to form P-DNA@1 and P-DNA@2 hybrids (Acuna, G. P. et al., ACS. Nano., 2012, 6, 3189), and quench the fluorescence of the FAM via a PET process (Goldberg, J. M. et al., J. Am. Chem. Soc., 2013, 135, 18651). In the fluorescence recovery step, the channel size of compound 1 and the large surface of compound 2 may play a critical role in effectively distinguishing P-DNA from DNA/RNA duplex. The single-strand moiety of P-DNA having smaller cross-sectional area but larger conformational flexibility should be able to "induced fit" to enter the pore and closely interact with the surface of compound 1 through multiple non-covalent interactions (Frieden, E., J. Chem. Educ., 1975, 52, 754). Furthermore, compounds 1 and 2 may have less affinity for DNA/RNA duplex because of the absence of unpaired bases and its rigid conformation. Therefore, the competitive hybridization of $T_{20}$ with the absorbed P-DNA would lead to the release of the FAM-labeled P-DNA from compounds 1 and 2 to form duplex DNA/RNA, resulting in the recovery of fluorescence. This is firstly supported by the changes of the fluorescence anisotropy (FA), a measure for the rotational motion-related factors of the P-DNAs, P-DNA@$T_{20}$ (hybrid duplex) before and after the addition of compounds 1 and 2 (Cao, Y. C. et al., Science, 2002, 297, 1536). As shown in FIGS. 11A and 11B, the addition of 1 and 2 into the P-DNA leads to an increase in the fluorescence anisotropy by factors 0.25 and 0.21, whereas a negligible influence on the P-DNA@$T_{20}$. This result reveals the exclusively stronger interaction of compounds 1 or 2 with the P-DNA than with hybrid duplex DNA/RNA. Secondly, agarose gel electrophoresis was carried out to further confirm this assertion. As shown in FIG. 12, P-DNA displayed one light band with a strong fluorescence. Such fluorescence is absent upon its incubation with compounds 1 and 2, suggesting that P-DNA can integrate with compounds 1 or 2 and the formed P-DNA@1 and P-DNA@2 systems are too large to pass through the gel (Guo, J. F. et al., RSC. Adv., 2014, 4, 9379). Once $T_{20}$ was introduced into the hybrids, the mixture yields two light bands. One band represents the hybrid duplex DNA/RNA which possesses higher molecular weight and moved slower, while the other one represents the remaining excessive, un-hybridized $T_{20}$. The identities of these two bands are verified by adding P-DNA to a solution containing excessive $T_{20}$. In such case, a bright and slower band corresponding to the duplex, and a light and faster band corresponding to the remaining excessive $T_{20}$, are observed (Liu, J. H. et al., Anal. Chem., 2013, 85, 1424). This experiment certificated that compounds 1 or 2 can distinguish P-DNA from hybrid duplex DNA/RNA and verified the proposed mechanism.

The invention claimed is:

1. A method of preparing a crystalline lanthanum-carboxylate coordination polymer, that method comprises steps of:
   (i) preparing a mixture comprising lanthanum ions and a pyridyl ligand which pyridyl ligand is a quaternized carboxylate pyridyl ligand and optionally subjecting the mixture to conditions under which a precipitate is formed and separating the precipitate; wherein the pyridyl ligand has a structure of Formula (V):

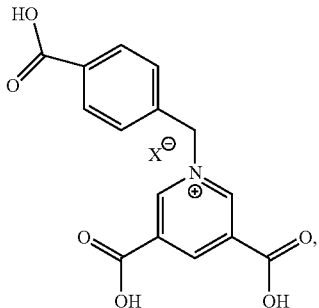

Formula (V)

wherein X is Br, Cl, or I;
   (ii) subjecting the mixture of step (i) or the precipitate of step (i) to conditions under which crystals of the lanthanum-carboxylate coordination polymer are formed;
   (iii) separating the crystals of the lanthanum-carboxylate coordination polymer from the mixture.

2. The method of claim 1, wherein step (i) comprises steps of:
   a) preparing a first pre-mixture comprising mixing the pyridyl ligand and a solvent;
   b) preparing a second pre-mixture comprising mixing a lanthanum salt and a solvent;
   c) adding the second pre-mixture to the first pre-mixture.

3. The method of claim 2, wherein the lanthanum salt is a hydrate of $La(NO_3)_3$ and wherein both of the solvent in step a) and the solvent in step b) independently comprise an aliphatic alcohol, water or a mixture thereof.

4. The method of claim 1 comprising steps of:
   (i) preparing a mixture comprising lanthanum ions and a pyridyl ligand which pyridyl ligand is a quaternized carboxylate pyridyl ligand and subjecting the mixture to conditions under which a precipitate is formed and separating the precipitate;
   (ii) subjecting the precipitate of step (i) to conditions under which crystals of the lanthanum-carboxylate coordination polymer are formed;
   (iii) separating the crystals of the lanthanum-carboxylate coordination polymer from the mixture;
and wherein step (ii) comprises steps of:
   a) adding a solvent, which solvent comprises water to the precipitate at a temperature of between about 20° C. and about 30° C.;
   b) allowing the mixture after step a) to stand at a temperature between about 20° C. and about 30° C. for at least about 72 hours for forming crystals of the lanthanum-carboxylate coordination polymer.

5. The method of claim 4, wherein subjecting the mixture to conditions under which a precipitate is formed in step (i) comprises stirring the mixture for between about 15 min and about 60 min for forming the precipitate and the precipitate is separated by filtration, and wherein step (i) further comprises a step of purifying the precipitate by washing with a washing solvent comprising an aliphatic alcohol.

6. The method of claim 1 comprising steps of:
   (i) preparing a mixture comprising lanthanum ions and a pyridyl ligand which pyridyl ligand is a quaternized carboxylate pyridyl ligand;
   (ii) subjecting the mixture of step (i) to conditions under which crystals of the lanthanum-carboxylate coordination polymer are formed;
   (iii) separating the crystals of the lanthanum-carboxylate coordination polymer from the mixture;
wherein step (ii) comprises steps of:
   a) stirring the mixture at a temperature of at least about 80° C. for about 15 min to about 60 min;
   b) filtering the mixture for obtaining a filtrate and a residue;
   c) allowing the filtrate to stand at a temperature of between 20° C. and 30° C. for at least about 72 hours for forming crystals of the lanthanum-carboxylate coordination polymer.

7. The method of claim 1, wherein step (iii) comprises steps of:
   a) separating the crystals from the mixture;
   b) purifying the crystals;
   c) drying the crystals.

* * * * *